US010463886B2

(12) United States Patent
Sverdlik et al.

(10) Patent No.: US 10,463,886 B2
(45) Date of Patent: Nov. 5, 2019

(54) TREATING WEAKENED VESSEL WALL SUCH AS VULNERABLE PLAQUE OR ANEURYSMS

(75) Inventors: Ariel Sverdlik, Tel-Aviv (IL); Shmuel Einav, Herzlia (IL); Zeev Aronis, Ashdod (IL); Ran Kornowski, Ramat-HaSharon (IL); Ifat Lavi, Neve Monoson (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 403 days.

(21) Appl. No.: 12/449,725

(22) PCT Filed: Feb. 21, 2008

(86) PCT No.: PCT/IL2008/000234
§ 371 (c)(1),
(2), (4) Date: Aug. 24, 2009

(87) PCT Pub. No.: WO2008/102363
PCT Pub. Date: Aug. 28, 2008

(65) Prior Publication Data
US 2010/0081933 A1 Apr. 1, 2010

Related U.S. Application Data

(60) Provisional application No. 60/902,495, filed on Feb. 22, 2007.

(51) Int. Cl.
*A61N 7/00* (2006.01)
*A61B 5/00* (2006.01)
(Continued)

(52) U.S. Cl.
CPC ............ *A61N 7/00* (2013.01); *A61B 5/0048* (2013.01); *A61B 8/485* (2013.01);
(Continued)

(58) Field of Classification Search
CPC ............ A61N 7/00; A61N 7/02; A61N 7/022; A61M 2205/3693
(Continued)

(56) References Cited

U.S. PATENT DOCUMENTS 4,867,962 A 9/1989 Abrams
5,053,006 A 10/1991 Watson
(Continued)

FOREIGN PATENT DOCUMENTS

WO WO 98/18393 5/1998
WO WO 98/26738 6/1998
(Continued)

OTHER PUBLICATIONS

Supplementary European Search Report and the European Search Opinion dated Mar. 4, 2011 From the European Patent Office Re. Application No. 08710234.9.
(Continued)

*Primary Examiner* — Tse W Chen
*Assistant Examiner* — Jason M Ip

(57) ABSTRACT

Described is a method of stabilizing blood vessel wall abnormality. The method includes ultrasonically heating at least a portion of the blood vessel wall having the abnormality; monitoring a parameter related to a property of at least a portion of the heated portion of the blood vessel wall; and stopping the heating when the monitored parameter changes by a predetermined factor or after the monitored parameter changes in a slow enough rate. The slow enough rate may be, for instance, a predetermined fraction of a maximal rate change observed during heating.

58 Claims, 12 Drawing Sheets
(1 of 12 Drawing Sheet(s) Filed in Color)

(51) Int. Cl.
*A61B 8/08* (2006.01)
*A61B 17/00* (2006.01)
*A61B 17/22* (2006.01)
(52) U.S. Cl.
CPC .............. *A61B 2017/00106* (2013.01); *A61B 2017/22001* (2013.01); *A61B 2017/22081* (2013.01); *A61N 2007/0078* (2013.01)
(58) Field of Classification Search
USPC ....... 600/407, 437, 438, 439, 462, 463, 466, 600/467, 468, 469; 604/22
See application file for complete search history.

(56) References Cited

U.S. PATENT DOCUMENTS

| | | | |
|---|---|---|---|
| 5,585,637 A | 12/1996 | Bertelsen et al. | |
| 5,921,954 A | 7/1999 | Mohr, Jr. et al. | |
| 6,026,317 A | 2/2000 | Verani | |
| 6,048,333 A | 4/2000 | Lennox et al. | |
| 6,083,170 A | 7/2000 | Ben-Haim | |
| 6,117,101 A | 9/2000 | Diederich | |
| 6,171,303 B1 | 1/2001 | Ben-Haim et al. | |
| 6,203,775 B1 | 3/2001 | Torchilin et al. | |
| 6,235,024 B1 | 5/2001 | Tu | |
| 6,375,668 B1 | 4/2002 | Gifford et al. | |
| 6,445,183 B1* | 9/2002 | Shimizu et al. | 324/309 |
| 6,475,210 B1 | 11/2002 | Phelps et al. | |
| 6,514,249 B1 | 2/2003 | Maguire et al. | |
| 6,626,855 B1 | 9/2003 | Weng et al. | |
| 6,669,687 B1 | 12/2003 | Saadat | |
| 6,736,809 B2 | 5/2004 | Capuano et al. | |
| 6,928,142 B2 | 8/2005 | Shao et al. | |
| 7,373,197 B2 | 5/2008 | Daighighian et al. | |
| 7,734,331 B2 | 6/2010 | Dhawale et al. | |
| 2002/0068864 A1 | 6/2002 | Bishop et al. | |
| 2002/0103429 A1 | 8/2002 | DeCharms | |
| 2003/0060813 A1* | 3/2003 | Loeb et al. | 606/17 |
| 2003/0147887 A1 | 8/2003 | Wang et al. | |
| 2004/0143449 A1 | 7/2004 | Behrenbruch et al. | |
| 2004/0144925 A1 | 7/2004 | Stoddart et al. | |
| 2005/0049487 A1 | 3/2005 | Johnson et al. | |
| 2005/0055053 A1 | 3/2005 | Phalen et al. | |
| 2005/0124892 A1* | 6/2005 | Weitzel et al. | 600/449 |
| 2005/0156115 A1 | 7/2005 | Kobayashi et al. | |
| 2006/0058711 A1 | 3/2006 | Harhen et al. | |
| 2006/0072799 A1 | 4/2006 | McLain | |
| 2006/0200119 A1 | 9/2006 | Vaska et al. | |
| 2007/0167940 A1* | 7/2007 | Stevens-Wright | 606/32 |
| 2008/0001090 A1 | 1/2008 | Ben-Haim et al. | |
| 2008/0230702 A1 | 9/2008 | Rousso et al. | |
| 2009/0304582 A1 | 12/2009 | Rousso et al. | |
| 2010/0121184 A1 | 5/2010 | Dhawale et al. | |
| 2010/0140483 A1 | 6/2010 | Rousso et al. | |
| 2012/0016273 A1 | 1/2012 | Diederich | |
| 2012/0106820 A1 | 5/2012 | Rousso et al. | |
| 2012/0172699 A1 | 7/2012 | Nagler et al. | |

FOREIGN PATENT DOCUMENTS

| | | |
|---|---|---|
| WO | WO 98/58588 | 12/1998 |
| WO | WO 99/53854 | 10/1999 |
| WO | WO 01/52930 | 7/2001 |
| WO | WO 03/020132 | 3/2003 |
| WO | WO 2005/030295 | 4/2005 |
| WO | WO 2005/076729 | 8/2005 |
| WO | WO 2008/102363 | 8/2008 |

OTHER PUBLICATIONS

International Preliminary Report on Patentability dated Oct. 29, 2009 From the International Bureau of WIPO Re.: Application No. PCT/IL2008/000234.

International Search Report dated Jan. 22, 2009 From the International Searching Authority Re.: Application No. PCT/IL2008/00234.
Written Opinion dated Jan. 22, 2009 From the International Searching Authority Re.: Application No. PCT/IL2008/000234.
Diederich et al. "Ultrasound Technology for Hyperthermia", Journal of Ultrasound in Medicine & Biology, 25(6): 871-887, 1999. Abstract.
Fujii et al. "Radiofrequency Induction Heating for the Treatment of Aortic Dissection in an Aminal Model", Journal of Cardiovascular Surgery, 41(5): 743-752, 2000. Abstract.
Golzarian et al. "Endoleakage After Endovascular Treatment of Abdominal Aortic Aneurysms: Diagnosis, Significance and Treatment", European Radiology, 2006. Abstract & Introduction.
Gunn et al. "Ultrasound as Treatment for Coronary Artery Disease", Echocardiography—International Cardiovascular Ultrasound & Allied Techniques, 18(3): 213-217, Apr. 2001. Abstract.
Kamineni et al. "Abdominal Aortic Aneurysm: A Review of Endoluminal Treatment", Journal of Interventional Cardiology, 17(6): 437-445, Nov. 11, 2004. Abstract.
O'Reilly et al. "Laser-Induced Thermal Occlusion of Berry Aneurysms: Initial Experimental Results", Radiology, 171(2): 471-474, 1989.
Sbarzaglia et al. "Interventional Techniques in the Treatment of Aortic Dissection", La Radiologia Medica, 111(4): 585-596, Jun. 2006. Abstract.
Uflacker et al. "Endovascular Treatment of Abdominal Aortic Aneurysms: A Review", European Radiology, 11: 739-753, 2001. Abstract.
Victal et al. "Left Ventricular Volume Reduction by Radiofrequency Heating of Chronic Myocardial Infarction in Patients with Congestive Heart Failure", Circulation, 105(11): 1317-1322, 2002.
Wright et al. "Denaturation of Collagen Via Heating: An Irreversible Rate Process", Annual Review of Biomedical Engineering, 4:109-128, Mar. 22, 2002. Abstract.
Translation of Notice of Reason for Rejection dated Mar. 15, 2013 From the Japanese Patent Office Re. Application No. 2009-550369.
Diederich et al. "Induction of Hyperthermia Using an Intrcavitary Multielement Ultrasonic Applicator", IEEE Transactions on Biomedical Engineering, 36(4): 432-438, Apr. 1989.
Advisory Action Before the Filing of an Appeal Brief dated Jul. 12, 2012 From the US Patent and Trademark Office Re. U.S. Appl. No. 11/667,793.
Communication Pursuant to Article 94(3) EPC dated Jun. 11, 2012 From the European Patent Office Re.: Application No. 06756259.5.
Communication Pursuant to Article 94(3) EPC dated May 12, 2010 From the European Patent Office Re. Application No. 06809851.6.
Communication Pursuant to Article 94(3) EPC dated May 29, 2012 From the European Patent Office Re. Application No. 05803689.8.
Communication Under Rule 71(3) EPC dated May 30, 2012 From the European Patent Office Re.: Application No. 02716285.8.
International Preliminary Report on Patentability dated Apr. 7, 2009 From the International Bureau of WIPO Re. Application No. PCT/IL2007/000918.
International Preliminary Report on Patentability dated Jan. 13, 2009 From the International Bureau of WIPO Re. Application No. PCT/IL2006/000834.
International Preliminary Report on Patentability dated May 14, 2008 From the International Bureau of WIPO Re. Application No. PCT/IL2006/001291.
International Preliminary Report on Patentability dated May 15, 2007 From the International Bureau of WIPO Re. Application No. PCT/IL2005/001173.
International Search Report dated Jul. 1, 2008 From the International Searching Authority Re. Application No. PCT/IL2006/000834.
International Search Report dated Jul. 2, 2007 From the International Searching Authority Re. Application No. PCT/IL2006/001291.
International Search Report dated Aug. 3, 2006 From the International Searching Authority Re. Application No. PCT/IL2005/001173.

(56) References Cited

OTHER PUBLICATIONS

International Search Report dated Oct. 15, 2008 From the International Searching Authority Re. Application No. PCT/2007/000918.
Official Action dated Nov. 1, 2010 From the US Patent and Trademark Office Re. U.S. Appl. No. 12/728,383.
Official Action dated Mar. 2, 2010 From the US Patent and Trademark Office Re. U.S. Appl. No. 11/980,617.
Official Action dated Dec. 8, 2010 From the US Patent and Trademark Office Re. U.S. Appl. No. 11/980,690.
Official Action dated Apr. 9, 2010 From the US Patent and Trademark Office Re. U.S. Appl. No. 11/798,017.
Official Action dated Aug. 13, 2008 From the US Patent and Trademark Office Re. U.S. Appl. No. 11/769,826.
Official Action dated Apr. 16, 2012 From the US Patent and Trademark Office Re.: U.S. Appl. No. 10/836,223.
Official Action dated Feb. 16, 2012 From the US Patent and Trademark Office Re. U.S. Appl. No. 11/747,378.
Official Action dated May 18, 2012 From the US Patent and Trademark Office Re. U.S. Appl. No. 11/989,223.
Official Action dated May 18, 2012 From the US Patent and Trademark Office Re. U.S. Appl. No. 12/514,785.
Official Action dated Apr. 19, 2012 From the US Patent and Trademark Office Re. U.S. Appl. No. 11/750,057.
Official Action dated Apr. 20, 2011 From the US Patent and Trademark Office Re. U.S. Appl. No. 11/798,017.
Official Action dated Dec. 20, 2011 From the US Patent and Trademark Office Re. U.S. Appl. No. 12/309,479.
Official Action dated Jun. 21, 2012 From the US Patent and Trademark Office Re. U.S. Appl. No. 12/309,479.
Official Action dated Sep. 21, 2009 From the US Patent and Trademark Office Re. U.S. Appl. No. 11/798,017.
Official Action dated Apr. 23, 2012 From the US Patent and Trademark Office Re. U.S. Appl. No. 11/932,987.
Official Action dated May 23, 2011 From the US Patent and Trademark Office Re. U.S. Appl. No. 11/980,690.
Official Action dated Jul. 30, 2012 From the US Patent and Trademark Office Re.: U.S. Appl. No. 11/980,683.
Official Action dated Sep. 30, 2010 From the US Patent and Trademark Office Re. U.S. Appl. No. 11/798,017.
Restriction Official Action dated Apr. 13, 2012 From the US Patent and Trademark Office Re. U.S. Appl. No. 11/989,223.
Bowsher et al. "Treatment of Compton Scattering in Maximum-Likelihood, Expectation-Maximization Reconstructions of SPECT Images", Journal of Nuclear Medicine, 32(6): 1285-1291, 1991.
Bracco Diagnostics "Cardiotec®: Kit for the Preparation of Technetium Tc 99m Teboroxime. For Diagnostic Use", Bracco Diagnostics Inc., Product Sheet, 2 P., Jul. 2003.
Bracco Diagnostics "Techneplex®: Kit for the Preparation of Technetium Tc 99m Pentetate Injection. Diagnostic—for Intravenous Use", Bracco Diagnostics™ Product Sheet, 5 P., Jun. 1995.
Dewaraja et al. "Accurate Dosimetry in 131I Radionuclide Therapy Using Patient-Specific, 3-Dimensional Methods for SPECT Reconstruction and Basorbed Dose Calculation", The Journal of Nuclear Medicine, 46(5): 840-849, May 2005.
Dittman "Radiolabeled Anti-CD20 Monoclonal Antibodies for the Treatment of B-Cell Lymphoma", Journal of Clinical Oncology, 20(16): 3545-3557, Aug. 15, 2002.
GE Healthcare "Myoview™: Kit for the Preparation of Technetium Tc99m Tetrofosmin for Injection. Diagnostic Radiopharmaceutical. For Intravenous Use Only. Rx Only", GE Healthcare, Product Sheet, 4 P., Aug. 2006.
Mallinckrodt "Kit for the Preparation of Technetium Tc 99m Sestamibi Injection", Mallinckrodt Inc., Product Sheet, 2 P., Sep. 8, 2008.
Mallinckrodt "OctreoScan®: Kit for the Preparation of Indium In-111 Pentetreotide. Diagnostic—for Intravenous Use. Rx Only", Mallinckrodt Inc., Product Sheet, 2 P., Oct. 25, 2006.
Pharmalucence "Kit for the Preparation of Technetium Tc99m Sulfur Colloid Injection for Subcutaneous, intraperitoneal, intravenous, and Oral Use", Pharmalucence Inc., Reference ID: 2977567, Prescribing Information, 10 P., Jul. 2011.
Saltz et al. "Interim Report of Randomized Phase II Trial of Cetuximab/Bevacizumab/Irinotecan (CBI) Versus Cetuximab/Bevacizumab (CB) in Irinotecan-Refractory Colorectal Cancer", Gastrointestinal Cancer Symposium, Hollywood, FL, USA, Jan. 27-29, 2005, American Society of Clinical Oncology, Abstract 169b, 4P., 2005.
Sands et al. "Methods for the Study of the Metabolism of Radiolabeled Monoclonal Antibodies by Liver and Tumor", The Journal of Nuclear Medicine, 28: 390-398, 1987.
Trikha et al. "Monoclonal Antibodies as Therapeutics in Oncology", Current Opinion in Biotechnology, 13: 609-614, 2002.
Volkow et al. "Imaging the Living Human Brain: Magnetic Resonance Imaging and Positron Emission Tomography", Proc. Natl. Acad. Sci. USA, 94: 2787-2788, Apr. 1997.
Translation of Notice of Reason for Rejection dated Sep. 25, 2012 From the Japanese Patent Office Re. Application No. 2009-550369.
Communication Pursuant to Article 94(3) EPC dated Dec. 2, 2011 From the European Patent Office Re. Application No. 08710234.9.
Translation of Notice of Reason for Rejection dated Aug. 16, 2013 From the Japanese Patent Office Re. Application No. 2009-550369.
European Search Report and the European Search Opinion dated Apr. 11, 2014 From the European Patent Office Re. Application No. 13195255.8.

\* cited by examiner

TREATING WEAKENED VESSEL WALL SUCH AS VULNERABLE PLAQUE OR ANEURYSMS

RELATED APPLICATIONS

The application is a National Phase Application of PCT Patent Application No. PCT/IL2008/000234 having International Filing Date of Feb. 21, 2008, which claims benefit under 35 U.S.C. § 119(e) from U.S. Provisional Patent Application No. 60/902,495, filed on Feb. 22, 2007. The contents of the above Applications are all incorporated herein by reference.

FIELD OF THE INVENTION

The invention relates to modifying the mechanical and/or biological properties of blood vessel walls, for example, for treating vulnerable plaque or aneurysms.

BACKGROUND OF THE INVENTION

Vulnerable plaques are atherosclerotic plaques causing in most cases mild to moderate narrowing of the arteries, and are comprised of a soft lipid core, and a very thin fibrous cap separating between the inner core and the lumen. The term "vulnerable" refers to the high tendency of these soft plaques to burst or rupture. Several factors may influence a plaque's stability and its tendency to rupture, including mechanical injury, inflammation, and infection. Progressive thrombosis and vasospasm may follow plaque rupture.

Mechanical stress acting on the thin cap, combined with insufficient support from the inner soft core, play an important role in plaque disruption. Once the thin cap ruptures, the thrombogenic content of the inner core is exposed to the blood circulation, initiating a thrombotic formation cascade that may occlude the arterial flow.

Repeated rupture and healing of a vulnerable plaque is one of the mechanisms, perhaps the dominant one, which creates artery stenosis. Moreover, a rupture of a plaque may lead to a direct arterial occlusion prior to any significant narrowing of the blood vessel.

Vulnerable plaques can be found in many blood vessels, including, but not limited to, coronary arteries; carotid arteries and peripheral arteries.

Most of the vulnerable plaques do not bulge inward. Instead, as a plaque grows, it often protrudes outward, into the wall of the artery, rather than into the channel-lumen where blood flows. In the following, vulnerable plaque is discussed as a plaque mass confined between a front surface, (also referred to as a cover or a cap), facing the inside of the blood vessel, and a back surface, forming part of the blood vessel and separating the blood vessel from its surroundings.

The term "Vulnerable Plaque" will refer in this document to any kind of rupture-prone plaque including, but not limited to coronary thin cap lipid reach plaques.

All types of atherosclerotic plaques with high likelihood of thrombotic complications and rapid progression are considered vulnerable plaques, as discussed in the article "From Vulnerable Plaque to Vulnerable Patient. A Call for New Definitions and Risk Assessment Strategies: Part I", Naghavi M., et al, *Circulation.* 2003; 108:1664-1672, the contents of which is incorporated herein by reference.

U.S. Pat. No. 6,475,210 (hereinafter US '210), the disclosure of which is incorporated herein by reference, describes treating vulnerable plaque by applying to it energy, which may be ultrasound energy. This reference refers to the vulnerable plaque as being made of a proteinic cap covering a lipid pool, and teaches congealing the lipid pool. Such congealing apparently requires heating the lipids to at least 85° C., according to the article "Structural Basis for Thermal Stability of Human Low-Density Lipoprotein", Jayaraman S., et al., *Biochemistry* 2005, 44, pp 3965-3971, the contents of which is incorporated herein by reference.

US patent application publication No. 2005-240249 (hereinafter US '249), the disclosure of which is incorporated herein by reference, seeks to provide heat to collagen of tissue to a temperature range of about 45° C. to 75° C. or higher for at least a few seconds to cause collagen to shrink a fraction of its original length.

US patent application publication No. 2003-0069525 (hereinafter US '525), the disclosure of which is incorporated herein by reference, teaches stabilizing atherosclerotic plaque by ultrasound heating to 47° C. or less, applied from outside the blood vessel.

An aneurysm is a localized, blood-filled dilation of a blood vessel. Aneurysms cavities are in many cases filled with blood thromboses (clots), generated due to relatively slow and circulatory blood flow inside the aneurysm cavity. Aneurysms are usually accompanied with thinning of the blood vessel wall.

Aneurysms most commonly occur in arteries at the base of the brain or in the aorta, The dilatation in a blood vessel can burst and lead to death at any time. The larger an aneurysm becomes, the more likely it is to burst. Current therapies include open surgery and endovascular stent-grafting. Some suggestions to treat aneurysm with heat were made, for instance, in U.S. Pat. Nos. 6,048,333; 6,375,668; U.S. Pat. No. 5,921,954; and PCT publication No. WO 99/53854.

In general, the absorption of ultrasonic energy in artery vessel wall is much bigger then in a blood thrombus (clot) and even bigger then in blood.

SUMMARY OF THE INVENTION

In the following, the term "blood vessel wall abnormality" will be used to refer collectively to conditions where a blood vessel wall is in particular risk for rupture or stenosis, and is susceptible to improvement upon biological or mechanical stabilization. Examples for such conditions include, for instance, vulnerable plaque and aneurysm. The term aneurysm encompasses, for instance, aortic aneurysm, thoracic aortic aneurysm, abdominal aortic aneurysm, cerebral aneurysm, and peripheral aneurysms.

An aspect of some embodiments of the invention relates to stabilizing blood vessel wall abnormality by heating the blood vessel having the abnormality as to achieve stabilization of the abnormality to an extent that reduces the risk associated with the abnormality. For example, reducing the risk of plaque rupture, or reducing the risk of aneurysm burst. In some embodiments the abnormality itself or a portion thereof is heated. The extent of stabilization may depend on the temperature to which the abnormality is heated and to the period of time, during which the abnormality is maintained in this temperature. Usually, higher temperatures require shorter heating times.

Changes in the mechanical properties of some parts of the vulnerable plaque, be it caused by heating or other methods, is sometimes collectively referred to herein as mechanical stabilization of the plaque. Similarly, Changes in the mechanical properties of some parts of the blood vessel wall at the aneurysm, be it caused by heating or other methods, is sometimes collectively referred to herein as mechanical stabilization of the aneurysm.

Changes in the chemical processes inside some parts of the vulnerable plaque, be it caused by heating or other methods, is sometimes collectively referred to herein as biological stabilization. Similarly, changes in the chemical processes inside some parts of the blood vessel wall at the aneurysm, be it caused by heating or other methods, is sometimes collectively referred to herein as biological stabilization of the aneurysm.

In accordance with some embodiments of the invention, stabilization is considered sufficient, and treatment is stopped, when a parameter monitored during treatment stops changing or starts changing more slowly. The monitored parameter is optionally related to the stabilization.

Changing more slowly may be for instance, a change that is slower by some predetermined portion from the fastest change monitored during treatment. Examples to predetermined portions include, for instance, 50%, 75%, 90%, 99%, and 99.9%. Optionally, the predetermined portion is at least 50% or at least any of the other above-mentioned examples of predetermined portions. Optionally, the treatment is stopped when the monitored parameter stops changing.

Optionally, changing pace is measured as an average over time, as to smooth out fluctuations.

An embodiment of the invention provides a method for treating vulnerable plaque, the method comprising identifying a vulnerable plaque, and heating the identified vulnerable plaque to achieve stiffening of the plaque to an extent that decrease it's vulnerability to rupture. Optionally, without damaging nearby tissue, for example, without congealing the lipids in the plaque-mass.

An embodiment of the invention provides a method for treating aneurysm, the method comprising identifying an aneurysm, and heating the identified aneurysm to achieve stiffening of the blood vessel wall at the aneurysm to an extent that decrease the probability that the aneurysm will burst without damaging nearby tissue.

Vulnerable plaque may be identified using imaging methods such as grayscale intravascular-ultrasound (IVUS), Spectral Analysis Intravascular Ultrasound, Optical Coherence Tomography (OCT), MRI, CT etc., that are capable of providing detailed data regarding the morphological and histological contents of the arterial wall.

By way of example, a vulnerable plaque may be detected by a light treatment catheter analogous to that described in US '210.

Alternatively, the vulnerable plaque may be detected from outside the blood vessel. For example, a device for detecting the vulnerable plaque may be positioned through an incision in the patient. The device may then detect the vulnerable plaque without the need for catheterization. During such a procedure, detection may be achieved during open surgery or in a minimally invasive manner. As another example, the vulnerable plaque may be detected from outside of the patient, such as with an imaging device (e.g., devices utilizing magnetic resonance, ultrasound, infra-red, fluorescence, visible light, radio waves, x-ray, etc.). Those skilled in the art will recognize that the strategy for detecting the vulnerable plaque may vary from the described methods. Numerous methods and devices for the detection of vulnerable plaque may be adapted for use with the present invention.

Aneurysms are much easier to detect and identify, and are many times detected accidently, when a patient is imaged for other reason. Aneurysms may be detected, for instance, by X-ray, ultrasound, or computed tomography (CT) scan.

Without being bound to theory, it is suggested that heating to a sufficient extent is heating to cause stiffening of the plaque or blood vessel wall because of substantial crosslinking of collagen. Substantial crosslinking is crosslinking that causes shrinkage of the collagen in the plaque or blood vessel wall to at most 70%, optionally at most 50% of the collagen's size before treatment. Plaque geometrical changes can be measured by some of the imaging technique used for its imaging and identification, supplying the clinician with morphometric data regarding the plaque's boundaries and its overall area and volume.

One way of determining that the blood vessel wall abnormality has been treated to be stiff enough is that value of ultrasound backscatter coefficient from the abnormality increased, in comparison to its value before treatment, in at least a predetermined factor. The predetermined factor may be any number not smaller than 5, for instance 5, 7, 10, 50, 100, 1000. Backscatter coefficient is defined and explained, for instance, in "Ultrasound properties of liver tissue during heating", Gertner M. R., et al, *Ultrasound in Med. & Biol.* Vol. 23, No. 9, pp. 1395-1403, 1997.

Another way to determine stiffness change in a blood vessel wall is by Ultrasonic Elastography, which is an imaging modality described, for instance, in Ophir J, et. al. "Elastography: a quantitative method for imaging the elasticity of biological tissues", published at Ultrasonic Imaging vol. 13, p. 111-134 1991.

In an exemplary embodiment of the invention, heating is applied using ultrasound, which may be applied to the plaque from inside the blood vessel, as described, for instance, by US '210, or from outside the blood vessel, as described, for instance, by US '525. The publications US '210 and US '525 enable a skilled person applying ultrasound to plaque, nevertheless, they do not teach using ultrasound in a manner which suffices to substantially crosslink the collagen in the plaque tissue without causing further damage to adjacent tissues, for instance, congealing the lipids in the plaque-mass.

The article "Aorta and Skin Tissues Welded by Near-Infrared $Cr^{4+}$:YAG Laser", Gayen T. K. et al, *Journal of Clinical Laser Medicine & Surgery*, Vol 21, Number 5, 2003 teaches that when blood vessel tissue is heated to 60-80° C., it is getting stiffer.

The article "Ultrasound properties of human prostate tissue during heating", by Worthington, A. E., et al, published in *Ultrasound in Med. & Biol.*, Vol. 28, No. 10, pp. 1311-1318, 2002, shows that heating tissue to 60-80° C. is accompanied with an increase of the US absorption and scattering from the treated region in the tissue.

Applicants realized that US heating of vulnerable plaque or blood vessel wall might be self-contained and the change in US absorption and backscatter that takes place at the target treated region, protects other parts at the vicinity of the target from over-heating, and may prevent heat damage to adjacent normal tissue. For example, if the US is applied with non-focused ultrasonic energy from inside the blood vessel lumen (by a catheter-like device), the most heated region will be near the cap of the plaque. When the collagen in the plaque tissues undergoes cross-linking, most of the ultrasonic energy will be reflected by the plaque tissue or absorbed by it, and much less energy will be transmitted to adjacent tissues. For instance, if the treated abnormality is vulnerable plaque in a coronary artery, US reflectance from cross-linked collagen in the cap may reduce or prevent excess heating of the heart muscle or the pericardium. Similarly, when treated abnormality is an abdominal aortic aneurysm, the crosslinking of the collagen in the aneurysm wall limits or prevents excess heating of adjacent esophagus or other organs adjacent to the external aortic wall in the aneurysm region.

Accordingly, in some embodiments of the invention, US heating is applied to vulnerable plaque to heat proteins in the plaque to between about 60° C. and about 80° C. for about 1 to 3 minutes. Similarly, in some embodiments of the invention, US heating is applied to aneurysm to heat proteins in the blood vessel wall to between about 60° C. and about 80° C. for about 1 to 3 minutes.

In an exemplary embodiment of the invention, the arterial wall abnormality is heated with US, and US backscatter and/or reflections from the plaque is detected. When the detected backscatter changes in a manner that indicates stiffening, for instance, when the backscatter increases by factor of 5 or more in respect of its value before treatment, ultrasonic sonication (ultrasonic energy transmission) is stopped. Optionally, the sonication is stopped automatically, with a closed-loop mechanism, which monitors reflection, and terminates heating upon detecting a predetermined change in the detected backscatter. The predetermined change is optionally a change in one or more of intensity, frequency, or any other ultrasound characteristic.

In some cases, cross-linking the collagen might be associated with shape change in the blood vessel. The shape change might include partial or whole occlusion of the blood vessel. In embodiments of the invention, a stent is deployed in the blood vessel to prevent occlusion of the blood vessel, to cause the stiffened blood vessel to have a desired final shape, to prevent releasing of a blood clot, or to be used for any usage of such stents that are known to the trained professional, like drug eluting stents.

In an embodiment of the invention, the stent is at least partially ultrasound-transparent, such that the stent may be deployed before ultrasound sonication. In some embodiments, the stent is heat conductive, and susceptible to heating by US, such that in practice, the US heats the stent and the stent heats the tissue behind it.

Additionally or alternatively, the stent has openings in a mesh-like structure, and the tissue sonication is done directly through these openings.

In other exemplary embodiments of the invention, the tissue is treated by ultrasonic energy as described in the embodiments in US '210 in general and that relate to FIGS. 2-7 in US '210, but with treatment parameters as described herein.

In other embodiments of the invention, the ultrasonic sonication is applied to plaque sites that are not considered rupture-prone, but are suspected to evolve to become rupture-prone plaques.

Thus, in accordance with an embodiment of the invention there is provided a method of stabilizing blood vessel wall abnormality, the method comprising:
  (a) ultrasonically heating at least a portion of the blood vessel wall having the abnormality;
  (b) monitoring a parameter related to a property of at least a portion of the heated portion of the blood vessel wall, and
  (c) stopping the heating when said parameter changes by a predetermined factor or after said parameter changes in a slow rate that is a predetermined fraction of a maximal rate change observed during heating.

Optionally, ultrasonically heating comprises heating at least a portion of the abnormality.

In an exemplary embodiment of the invention, the heating is configured to cause at least a portion of the collagen in the heated blood vessel wall 100% cross-linking.

Optionally, the heating is to a temperature of 60-80° C.

In an exemplary embodiment of the invention, the parameter is related to the stiffness of a portion of the blood vessel.

Optionally, the parameter is ultrasound reflection.

Optionally, the parameter is ultrasound backscatter.

In an embodiment of the invention, the parameter is related to cross-linking degree of collagen in at least a portion of the heated abnormality.

In one embodiment, monitoring comprises elastography, for instance, ultrasound elastography.

Optionally, stabilizing comprises mechanical stabilization. Alternatively or additionally, stabilizing comprises biological stabilization.

Optionally, monitoring the property comprises magnetic resonance imaging.

Optionally, the treated blood vessel is an artery.

Optionally, the abnormality is vulnerable plaque.

Optionally, the abnormality is aneurysm.

In an embodiment of the invention, the heating causes full cross-linking of collagen in at least a portion of the heated blood vessel wall.

In an embodiment, the heating causes at least 50% of the blood vessel abnormality collagen to shrink in at least 50% of its length before heating.

Opionally, the heating causes at least 50% of the blood vessel abnormality collagen maximal shrinking.

In an exemplary embodiment of the invention, ultrasonically heating comprises stiffening of a vulnerable plaque tissue as to decrease the plaque vulnerability to rupture.

In an embodiment of the invention, ultrasonically heating comprises stiffening of aneurysm tissue so as to decrease the tendency of the aneurysm to rupture.

Optionally, ultrasonically heating comprises reducing the aneurysm diameter.

In an exemplary embodiment, ultrasonically heating comprises noninvasively applying ultrasound to the blood vessel abnormality.

Optionally, noninvasively applying ultrasound to the blood vessel comprises focusing ultrasound radiation on a portion of said blood vessel.

Optionally, noninvasively applying ultrasound to the blood vessel comprises invasively applying ultrasound radiation on a portion of said blood vessel, optionally from within the blood vessel having the abnormality.

In an embodiment of the invention, the method comprises deploying a stent in the blood vessel.

Optionally, said deploying is before said heating.

Optionally, heating is for a period of between 0.1 and 1000 seconds.

Optionally, heating is for a period of between 15 and 600 seconds.

Optionally, heating is for a period of between 30 and 300 seconds.

Optionally, heating is for a period of at least 20 seconds.

Optionally, heating is for a period between 20 and 60 seconds.

There is also provided by an embodiment of the present invention an apparatus for treating blood vessel wall comprising:
  a catheter;
  an ultrasound emitter mounted on the catheter and adapted for emitting ultrasound at a portion of the blood vessel wall;
  a receiver mounted on the catheter and adapted for receiving ultrasound; and
  a controller,
wherein the controller is configured to stop ultrasound emission by the emitter upon receiving ultrasound signal with a predetermined parameter by the receiver.

In an embodiment of the invention, the receiver is an ultrasound receiver.

In an embodiment, the predetermined parameter is a ratio between intensity of a currently received signal and intensity of received ultrasound before treatment.

In an embodiment of the invention, the predetermined parameter is a ratio between a rate at which a received signal is changing last received and a rate at which a received signal was changing earlier in treatment.

Optionally, the ultrasound emitter and receiver are the same.

Optionally, n a single ultrasound transducer is configured to cyclically receive and emit ultrasound.

Optionally, the ultrasound emitter is configured to emit ultrasound in frequencies of 1-50 MHz.

Optionally, the apparatus comprises a manual control, configured to allow a user to control ultrasound emission parameters and/or ultrasound detection parameters.

Optionally, the manual control is configured to allow a user to stop ultrasound emission.

In an embodiment, the apparatus is configured to provide treatment in predetermined power/time settings, so as to stiffen a wall of the blood vessel.

Optionally, the apparatus is configured to provide treatment in predetermined power/time settings, so as to block vasa vasorum.

There is also provided by an embodiment of the present invention a method of treating a subject, the method comprising:

(a) identifying vulnerable plaque in a blood vessel of the subject, the vulnerable plaque comprising a lipid pool and a cap; and (b) ultrasonically heating said vulnerable plaque without congealing the lipid pool.

In an exemplary embodiment, the vulnerable plaque comprises collagen, and said heating fully cross-links at least a portion of said collagen.

There is further provided according to an embodiment of the invention, a method of treating a subject, the method comprising:

(a) identifying blood vessel abnormality in a blood vessel of the subject; and (b) stabilizing said abnormality using an apparatus as described above.

There is further provided according to an embodiment of the invention, a method of treating a subject, the method comprising:

(a) identifying a blood vessel abnormality in a blood vessel of the subject; and (b) stabilizing said abnormality using a method according to any of the methods described above.

Optionally, the abnormality comprises vulnerable plaque.

Optionally, the abnormality comprises aneurysm.

Optionally, treating comprises reducing a risk of artery stenosis.

BRIEF DESCRIPTION OF FIGURES

The patent or application file contains at least one drawing executed in color. Copies of this patent or patent application publication with color drawing(s) will be provided by the Office upon request and payment of the necessary fee.

Non-limiting examples of embodiments of the present invention are described below with reference to figures attached hereto and listed below. Identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION OF EXEMPLARY EMBODIMENTS

Overview of a Treatment Method

In an exemplary embodiment of the invention, a treating method comprises identifying vulnerable plaque. Vulnerable plaque may be identified using imaging methods such as grayscale intravascular-ultrasound (IVUS), Spectral Analysis Intravascular Ultrasound, Optical Coherence Tomography (OCT), MRI, CT etc., that are capable of providing detailed data regarding the morphological and histological contents of the arterial wall.

By way of example, a vulnerable plaque may be detected by a light treatment catheter of the kind described in US '210.

Alternatively, the vulnerable plaque may be detected from outside the blood vessel. For example, a device for detecting the vulnerable plaque may be positioned through an incision in the patient. The device may then detect the vulnerable plaque without the need for catheterization. During such a procedure, detection may be achieved during open surgery or in a minimally invasive manner. As another example, the vulnerable plaque may be detected from outside of the patient, such as with an imaging device (e.g., devices utilizing magnetic resonance, ultrasound, infra-red, fluorescence, visible light, radio waves, x-ray, etc.). Those skilled in the art will recognize that the strategy for detecting the vulnerable plaque may vary from the described methods.

Numerous methods and devices for the detection of vulnerable plaque may be adapted for use with the present invention.

FIGS. 1-5 depict embodiments of the invention in the context of treating vulnerable plaque; and FIGS. 6-10 depict embodiments of the invention in the context of treating aneurysms.

Although drawings are provided only for treating these two abnormalities, various embodiments of the invention are useful in treating other prone to failure wall vessel abnormalities.

Figure 1:
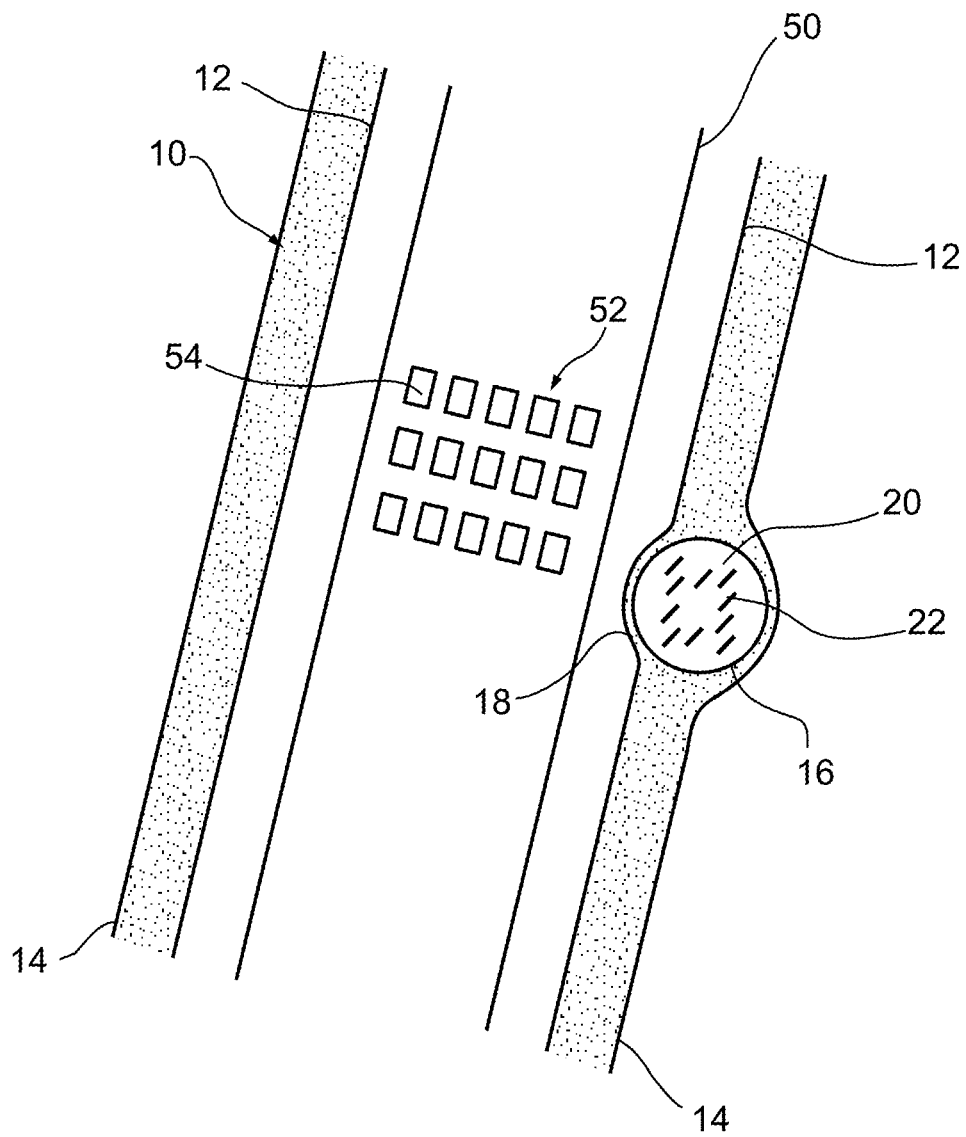
FIG. 1 is a schematic illustration of a blood vessel with vulnerable plaque during treatment according to an embodiment of the invention FIG. 2 schematically illustrates the blood vessel of FIG. 1 after treatment according to an embodiment of the invention.

FIG. 1 is a schematic illustration of a blood vessel (10) having an inner surface (12) and an outer surface (14) also known as adventitia. The lumen of the blood vessel is defined by inner surface 12. Along a portion of the circumference of blood vessel 10 there is shown a vulnerable plaque (16). Vulnerable plaques usually protrude out of the back surface of the blood vessel much more than of the front surface. Vulnerable plaque 16 is shown to include a cap 18 and mass 20. The cap is in the boundary between the plaque's soft thrombogenic core 20 and the blood vessel lumen, and it contains mainly collagen. The cap is made of fibrotic tissue. The mass of the plaque (20) is not uniform but is made of patches of different tissues like fibro-fatty, fibrotic, calcified and necrotic regions (22)

Also shown in FIG. 1 is a catheter (50), carrying an array (52) of ultrasound elements 54. To stabilize vulnerable plaque 16, Ultrasound is emitted from at least the elements that face the plaque. In an embodiment of the invention, the target of the ultrasonic heating is the vasa vasorum of the plaque, located inside the plaque mass and in the adventitia 14 of blood vessel 10.

The inventors realized that targeting the adventitia may be particularly helpful in stabilizing vulnerable plaque, because some of the biological processes that make vulnerable plaque more prone to rupture take place in the adventitia.

In particular, vulnerable plaque development is facilitated by the angiogenesis of vasa vasorum into the plaque. The vasa vasorum form a network of tiny blood vessels that feed the cells inside the plaque tissue and cause blood hemorrhages inside the plaque. These hemorrhages increase the plaque's vulnerability. Accordingly, in an exemplary embodiment of the invention, heating is configured to block the vasa vasorum inside the plaque tissue volume.

Targeting optionally comprises focusing ultrasonic energy. Focusing US energy is described, for instance, in U.S. Pat. No. 5,906,580 and Patent Application Publication Nos. 2006/058678 and 2007/016039 (focusing ultrasound applied non-invasively from outside the body) and US Patent Application Publication 2006/0224090 (focusing with an ultrasound catheter).

Alternatively or additionally, targeting comprises heating so as to allow blood flow to efficiently cool non-targeted tissue.

Optionally, one or more of the elements 54 is used as a receiver, receiving ultrasound energy reflected (and/or scattered) from cap 18 of plaque 16, to allow monitoring and control of the stabilization process. Optionally, treatment and monitoring are carried out on separate times, for instance: each 1 sec of treatment is followed with 50 msec of monitoring, during which treatment is paused. When received ultrasound energy is indicative of sufficient stiffening of the plaque, US emission may be stopped, and the catheter 50 is moved along the blood vessel, optionally, in order to identify other vulnerable plaques, and/or stabilize them. Although an array of ultrasound elements is illustrated in the figures, the invention may be practiced with a single emitter and a single receiver.

Figure 2:
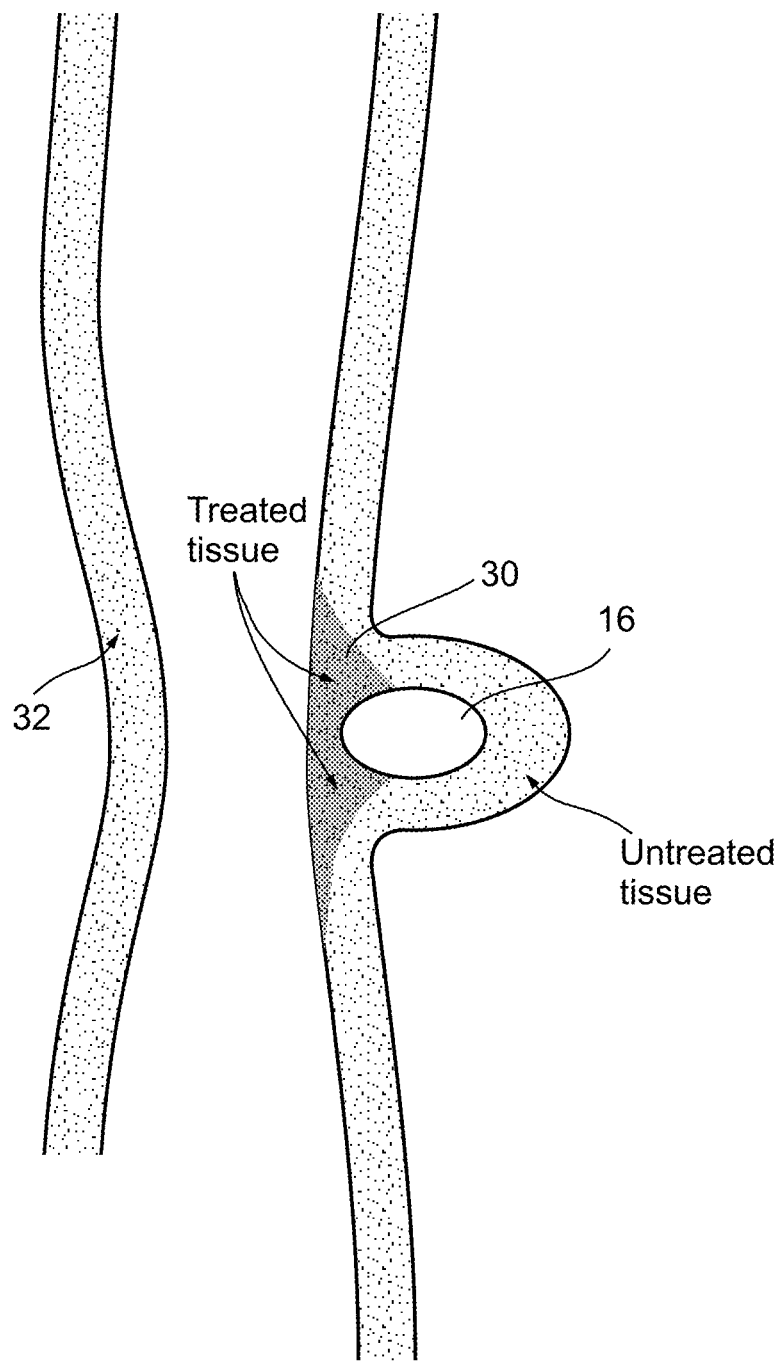

FIG. 2 shows the blood vessel of FIG. 1 after treatment. Plaque 16 is shown to remain as a separate entity inside the blood-vessel wall, having well-defined borders. The plaque may change its orientation, because, tissue 30, which is nearest to the ultrasonic transducer undergoes the largest shrinking, and this shrinking squeezes the plaque from near the transducer away from the transducer. This shrinking also causes an untreated blood vessel portion (32) facing the treated one to get closer to the treated tissue (30) and this way the diameter of the blood vessel is reduced in the vicinity of the treated plaque.

In some cases, there may be a risk that the reduction in blood vessel diameter leaves the blood vessel too narrow to allow normal blood flow therethrough. In some cases, there may be a risk of complete occlusion of the blood vessel due to the shrinkage of collagen in the plaque. In these, and possibly other cases, it may be advisable to support the blood vessel, for instance, with a stent, during stabilizing the plaque.

Figure 3:
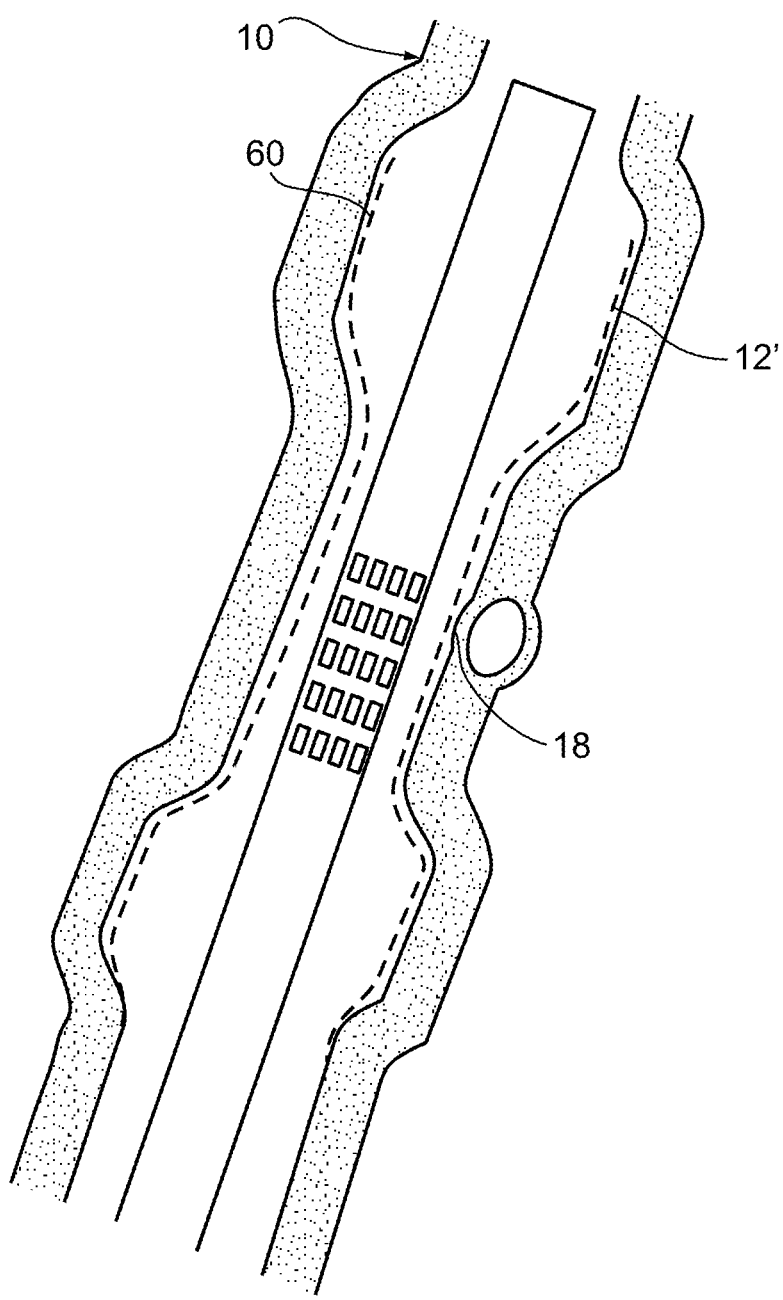
FIG. 3 schematically illustrates a blood vessel with a stent 60 supporting it during treatment according to an embodiment of the invention.

FIG. 3 shows blood vessel 10 with a stent 60 supporting it during treatment. Optionally, the stent is deployed to support the blood vessel in plaque-free areas (12'), without contacting the cap (18) of the plaque, to avoid any chance of rupture of the plaque by the stent.

Figure 4:
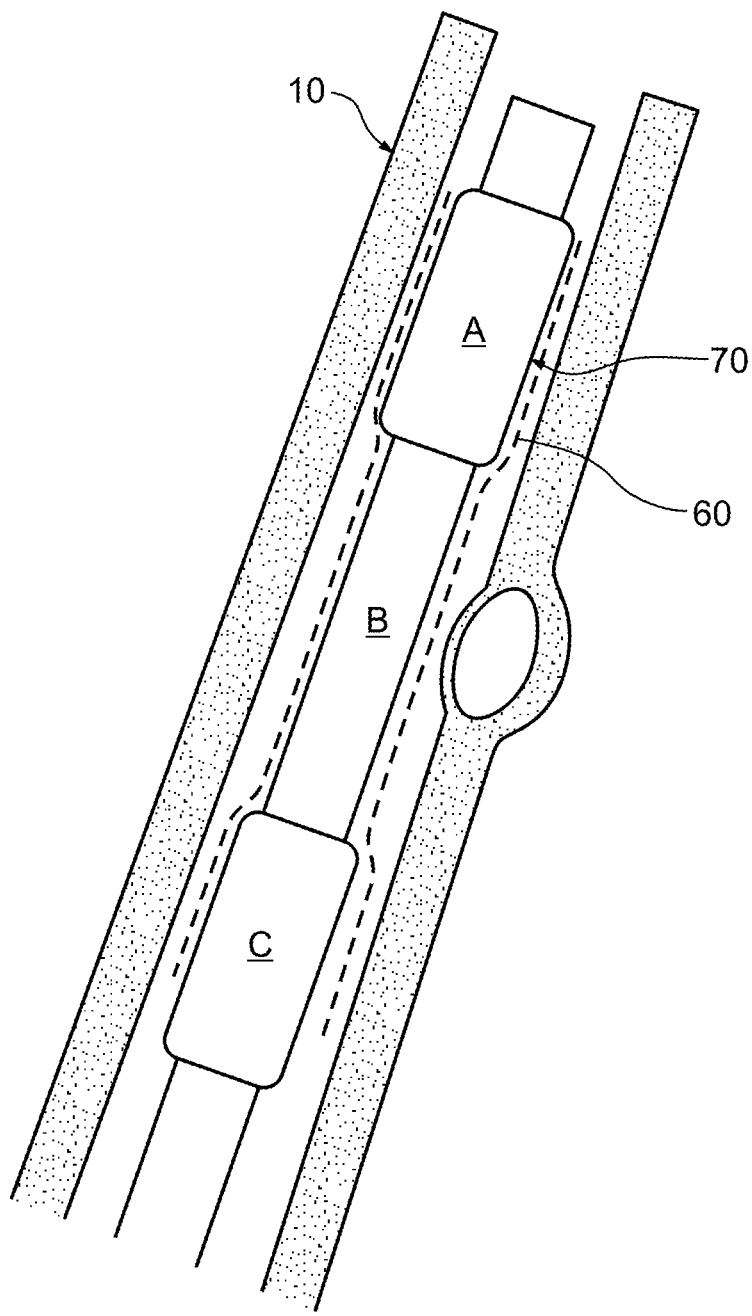
FIG. 4 schematically illustrates vulnerable plaque treatment utilizing a balloon according to an embodiment of the invention.

Optionally, deployment of stent 60 is carried out as depicted in FIG. 4, which schematically shows a balloon 70, having three portions (A, B, and C). Portion B is of smaller diameter than portions A and C, and thus expands stent 60 to a lesser extent. Optionally, at this stage, the balloon 70 is shrunk and withdrawn from the blood vessel, and catheter 50 is inserted to stabilize the plaque as shown in FIG. 3. Alternatively, US transmitters are inside balloon 70, and heat the plaque through the balloon surface.

Figure 5:
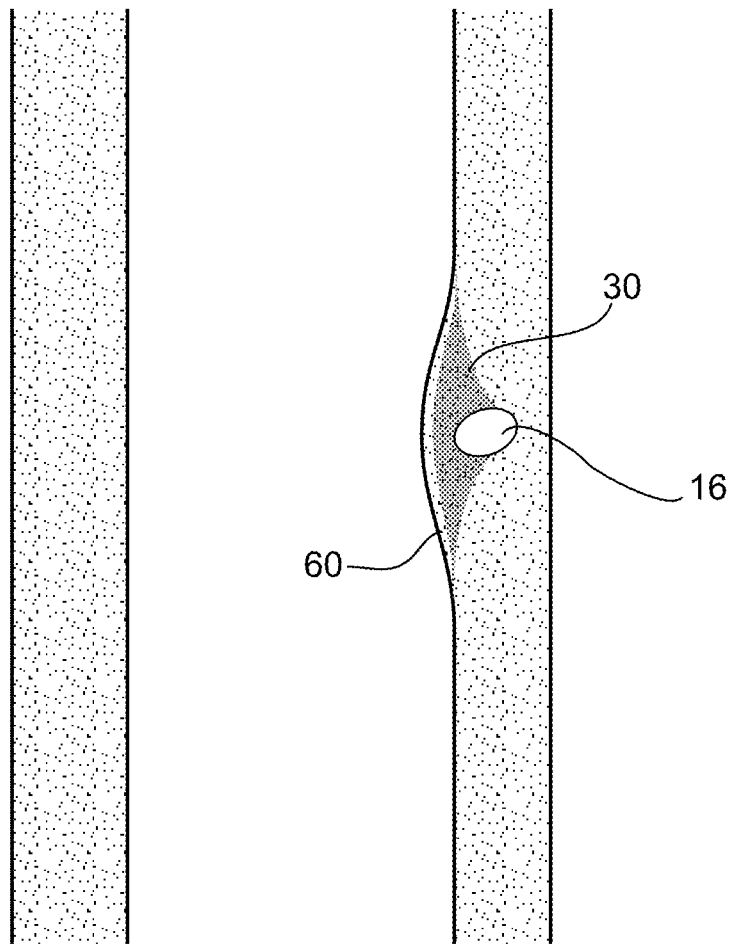
FIG. 5 schematically illustrates the blood vessel of FIG. 1 after stent-assistant treatment according to an embodiment of the invention.

FIG. 5, similarly to FIG. 2, shows a blood vessel after a treatment which utilizes a stent 60. As in FIG. 2 plaque 16 is shown to remain as a separate entity inside the blood-vessel wall, having well-defined borders and different orientation than it had before treatment. The orientation may be different, because tissue 30, which is nearest to the ultrasonic transducer undergoes the largest shrinking, and this shrinking squeezes the plaque from near the transducer away from the transducer. Stent 60 prevents the diameter of the blood vessel from being reduced in the vicinity of the treated plaque. In some embodiments, the stent does not prevent diameter reduction of the blood vessel, but controls it to be small enough not to interrupt blood flow in the vessel in a dangerous degree.

Figure 6:
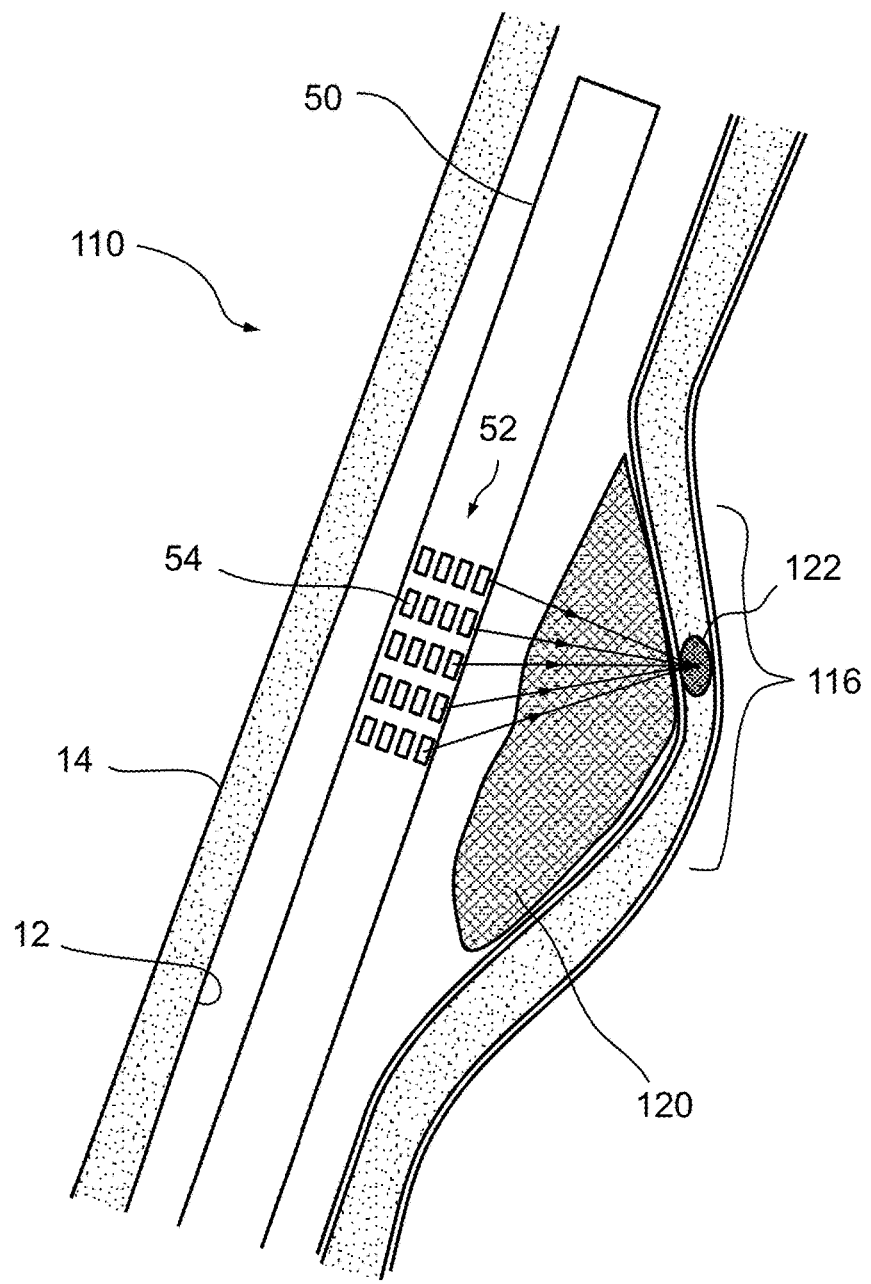
FIG. 6 is a schematic illustration of a blood vessel with aneurysm during treatment according to an embodiment of the invention FIG. 7 schematically illustrates the blood vessel of FIG. 6 after treatment according to an embodiment of the invention.

FIG. 6 is a schematic illustration of a blood vessel (110) having an inner surface (12) and an outer surface (14). The lumen of the blood vessel is defined by inner surface 12. Along a portion of the circumference of blood vessel 110 there is shown an aneurysm (116). Aneurysm 116 is shown to hold a blood clot 120. The ultrasonic absorption coefficient of blood clots is smaller than that of blood vessel walls, therefore, blood clots heat by ultrasound less than blood vessel walls.

Also shown in FIG. 6 is a catheter (50), carrying an array (52) of ultrasound elements 54. To stabilize aneurysm 116, Ultrasound is emitted from at least the elements that face the anneurysm. Optionally, one or more of the elements 54 is used as a receiver, receiving ultrasound energy reflected (and/or scattered) from aneurysm 116 to allow monitoring and control of the stabilization process.

Optionally, the ultrasound is focused to a treatment focus 122. Alternatively, no focusing is applied. Means suitable for such focusing are, by themselves, known in the art and available a person of ordinary skill.

Figure 7:
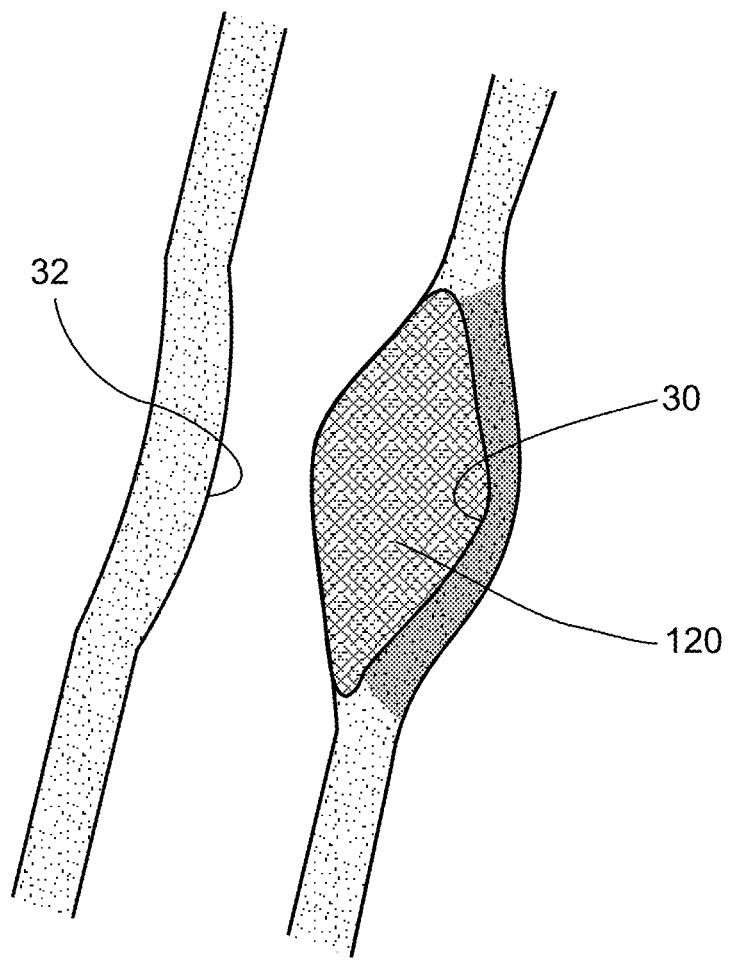

FIG. 7 shows the blood vessel of FIG. 6 after treatment. Blood clot 120 is shown to remain as a separate entity attached to the blood-vessel wall, having well-defined borders. Because tissue 30, on which ultrasound was focused shrinks and stiffens due to collagen cross-linking, tissue 30 pushes blood clot 120 into the blood vessel lumen. This shrinking may also cause an untreated blood vessel portion (32) facing the treated one to get closer to the treated tissue (30) and this way the diameter of the blood vessel is reduced in the vicinity of the treated plaque.

In some cases, there may be a risk that the reduction in blood vessel diameter leaves the blood vessel too narrow to allow normal blood flow therethrough. In some cases, there may be a risk of complete occlusion of the blood vessel due to the shrinkage of collagen in the vessel wall. In some cases, there may be a risk that the blood clot will escape into the blood stream. This may be dangerous to the patient, as it might cause a disruption or blocking of the blood flow downstream. To prevent blood clot escape and possibly for other reasons, it may be advisable to support the blood vessel, for instance, with a stent, during and/or after aneurysm stabilization. Optionally, after the treatment, the patient is administered thrombolysis agents to dissolve clot 120.

Figure 8:
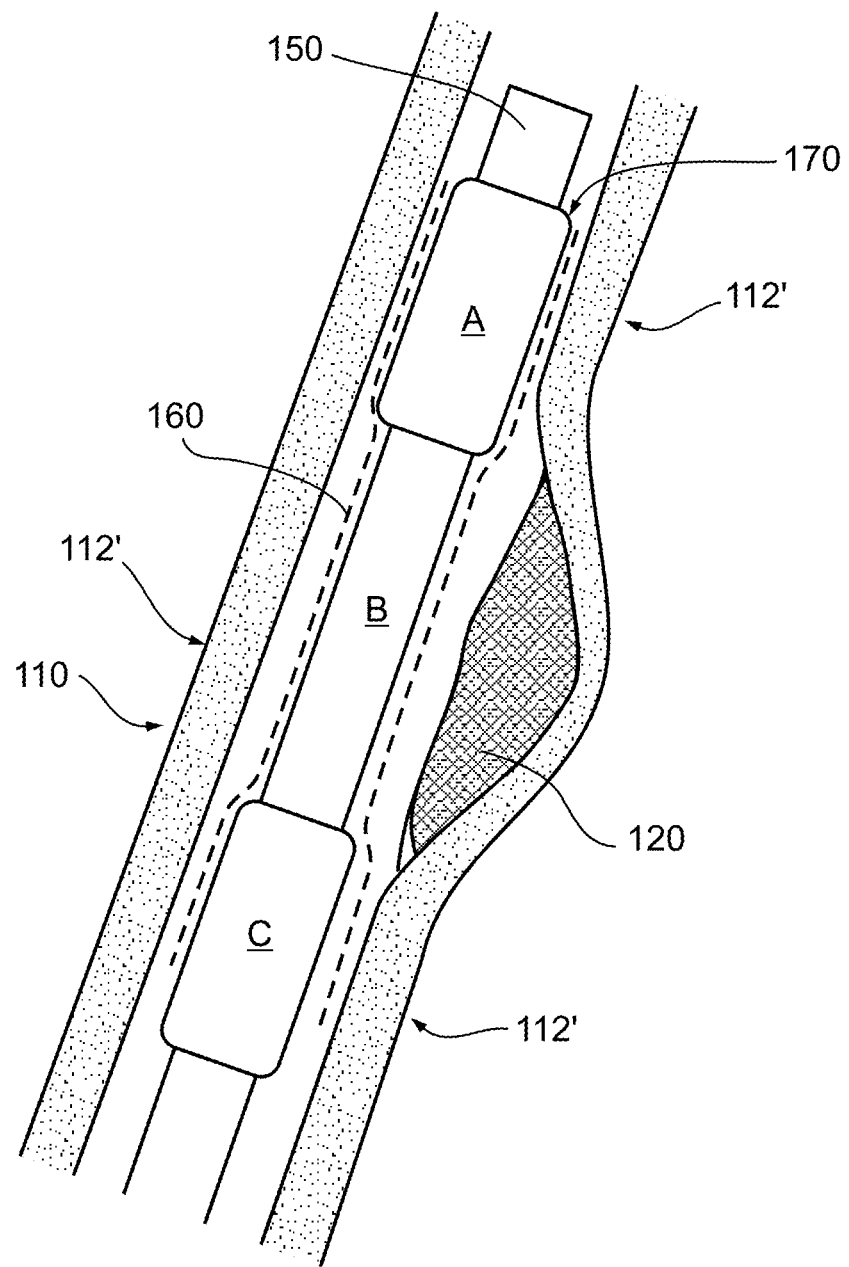
FIG. 8 schematically illustrates aneurysm treatment utilizing a balloon according to an embodiment of the invention.

FIG. 8 shows blood vessel 110 with a stent 160 supporting it during treatment. Optionally, the stent is deployed to support the blood vessel in aneurysm-free areas (112'), to prevent occlusion of the blood vessel while leaving room for geometry changes in the clot. Optionally, the stent is deployed to prevent escape of blood clot 120 into the lumen of blood vessel 110.

Optionally, stent 160 is deployed as depicted in FIG. 8, which schematically shows a balloon 170, having three portions (A, B, and C). Portion B is of smaller diameter than portions A and C, and thus expands stent 160 to a lesser extent as to allow room for blood clot 120. Optionally, at this stage, the balloon 170 is shrunk and withdrawn from the blood vessel, and catheter 150 is inserted to stabilize the aneurysm as shown in FIG. 7. Alternatively, US transmitters are inside balloon 170, and heat the plaque through the balloon surface.

Figure 9:
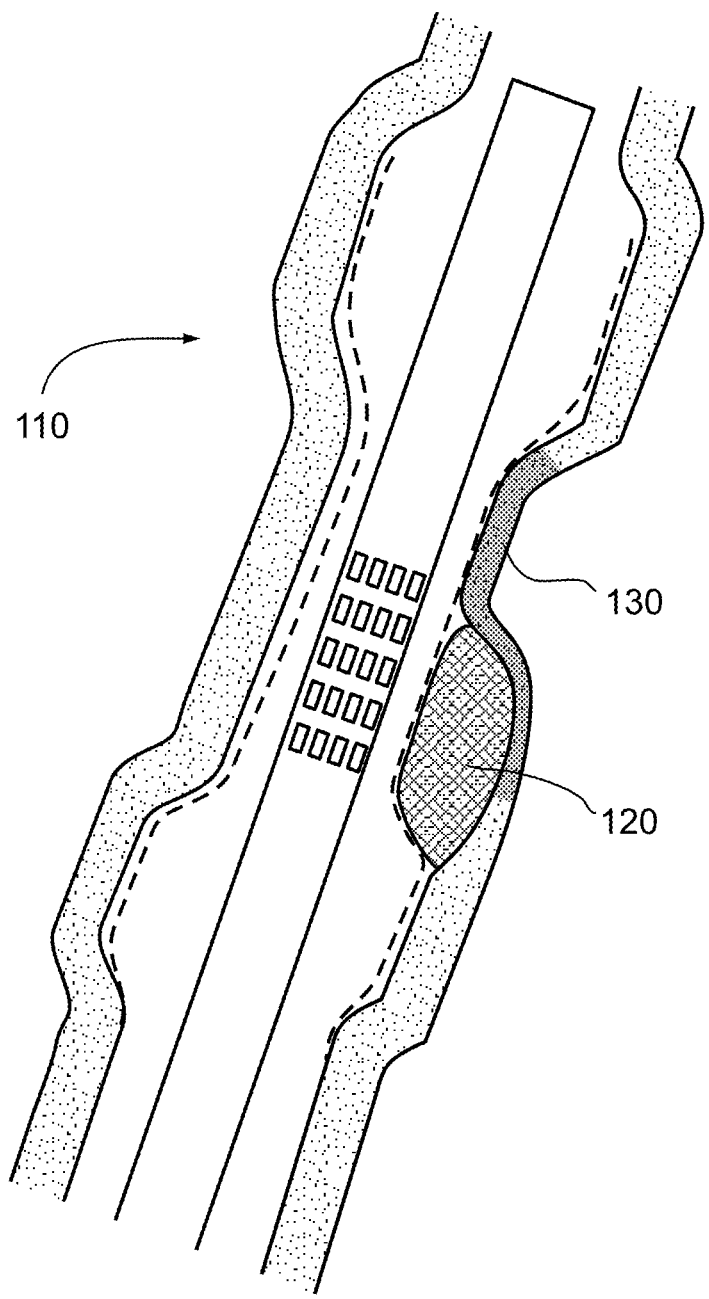
FIG. 9 schematically illustrates the blood vessel of FIG. 6 after stent-assistant treatment according to an embodiment of the invention.

FIG. 9 shows a blood vessel after a stent-assistant treatment. Stent 160 prevents clot 120 from escaping into the lumen of blood vessel 110. In some embodiments, treated tissue 130 changes geometry in response to the treatment, and stent 160 limits the shrinking into the blood vessel lumen.

Stabilization Methods

Figure 10:
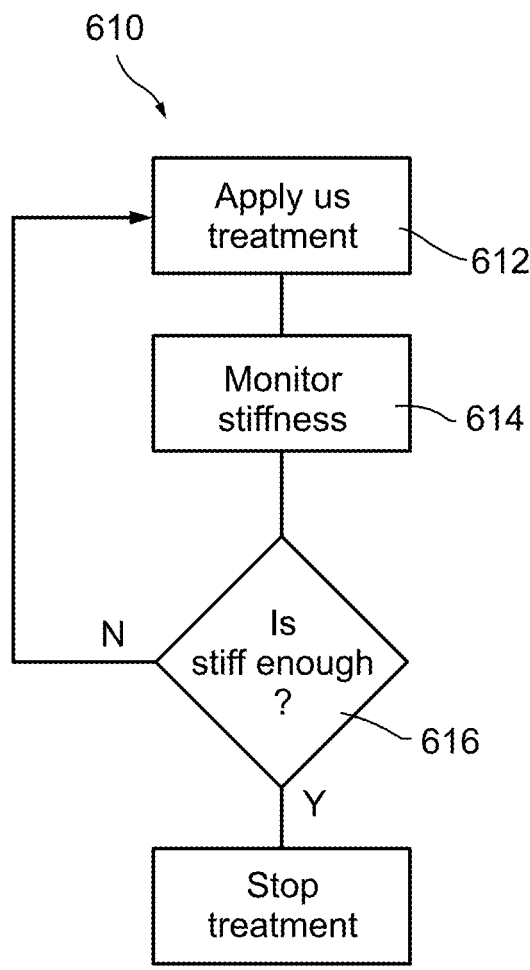
FIG. 10 is a flowchart of actions to be taken in carrying out a method for treating vulnerable plaque in accordance with an embodiment of the invention.

FIG. 10 is a flowchart of a method 610 of treating blood vessel wall abnormality, for example, vulnerable plaque and/or aneurysm, in accordance with an embodiment of the invention. The method 610 includes applying to the abnormality ultrasound radiation (612), monitoring treatment progression (614), deciding, based on monitor results, if sufficient stiffness achieved (616), and if so, stopping the radiation (618).

Optionally, monitoring treatment progression comprises monitoring stiffness-related parameters. Optionally, monitoring stiffness-related parameter comprises monitoring stiffness using ultrasonic elastography.

Additionally or alternatively, monitoring treatment progression comprises detecting ultrasound radiation reflected or otherwise backscattered from the vulnerable plaque or from the aneurysm. For instance, when backscatter stops changing, full cross-linking is indicated, and further heating have very little therapeutic value, if at all.

Optionally, ultrasound heating is applied non-invasively, from outside the body.

Optionally, ultrasound heating is applied invasively, from within the treated blood vessel.

Optionally, ultrasound heating is applied invasively, from outside the treated blood vessel, for instance through a surrounding tissue.

Optionally, ultrasound backscatter is monitored non-invasively. Ultrasound backscatter detection that may be applied non-invasively in an embodiment of the invention is described in the article of Gertner, cited above. Alternatively or additionally, ultrasound backscatter detection is with an US catheter.

Optionally, backscatter detection and ultrasound heating is carried out with the same ultrasound device. Alternatively, two different devices are used.

Optionally, both heating and detecting are non-invasive.

Optionally, both heating and detecting are invasive.

Optionally, heating is invasive and detecting is non-invasive.

Optionally, heating is non-invasive, and detecting is invasive.

Optionally, monitoring treatment progression comprises detecting changes in stiffness of a specific targeted tissue. Optionally the targeted tissue is only a portion of the treated tissue.

In an embodiment of the invention, monitoring tissue progression comprises monitoring changes that take place in the adventitial; for example, monitoring ultrasound backscatter from the adventitia.

In an embodiment of the invention, monitoring treatment progression comprises monitoring changes that take place in the vasa vasorum; for example, monitoring ultrasound backscatter from the vasa vasorum.

In an embodiment of the invention, monitoring tissue progression comprises monitoring changes that take place in the plaque's cap; for example, monitoring ultrasound backscatter from the cap.

Optionally, monitoring treatment progression includes detecting changes in the tissue properties using modalities such as grayscale intravascular-ultrasound (IVUS), Spectral Analysis Intravascular Ultrasound, Optical Coherence Tomography (OCT), MRI, CT etc., that can provide detailed data regarding the morphological and histological contents of the arterial wall.

In an embodiment of the invention, heating is stopped when at least a portion of the blood vessel undergoes a desired mechanical or biological modification. Examples to kinds of mechanical modifications include stiffening, shortening, and thickening. Some of the above examples may result from protein cross-linking and/or denaturation in the tissue, for example, collagen cross-linking. Examples of biological modifications include blocking of intra-plaque vasa vasorum, and extinction of inter-plaque macrophages.

Optionally, the heating is stopped only when the desired modification is full. A modification is considered full when further heating does not result in further modification. Optionally, a parameter related with the modification is monitored, and heating is stopped when the parameter stops changing.

Parameters responsive to tissue stiffness may be obtained, from example, using ultrasound reflection, ultrasound backscatter, by ultrasound elastography, or other kinds of elastography.

Parameters responsive to cross-linking degree may be obtained, for example, using magnetic imaging.

In an embodiment of the invention, heating is stopped when at least a certain portion of the collagen volume in a target tissue undergoes 100% cross-linking. In an embodiment of the invention, cross-linking is considered full (that is, 100% cross-linking) when further heating does not change the degree of cross-linking. Optionally, cross-linking is considered full when a parameter responsive to the cross-linking stops changing. Optionally, cross-linking is considered full when such a parameter changes considerably, for instance, by factor of 5 or more. Optionally, the certain portion that undergoes full cross-linking is any portion between about 50% to about 100%, for example 50%, 60%, 70%, 80%, 90%, or 100%. The greater is the cross-linked portion—the better is the stabilization of the vulnerable plaque. However, in some clinical circumstances, cross-linking less than 100% of the collagen may be preferred.

Optionally, cross-linking degree is first experimentally evaluated, for example, ex vivo, and ultrasound protocols resulting in desired effects are compiled in accordance with the results obtained. Optionally, ultrasound applicators are configured to apply therapy in accordance with one or more of the compiled protocols. In an embodiment of the invention, the compiled protocols are scaled by the amount of ultrasound absorbed in the tissue, and the applicators are configured to apply the protocols responsive to data received on ultrasound absorption in the treated tissue. It should be noted that at least with blood vessel wall abnormalities, such as vulnerable plaque and aneurysms, attenuation of the ultrasound is mainly due to absorption. Accordingly, in an embodiment of the invention, the ultrasound applicator is configured to apply the protocols responsive to data received on ultrasound attenuation, which many times is easier to measure.

Optionally, the same probe used for heating the blood vessel wall abnormality with ultrasound is also used for monitoring the reflected ultrasound. In an embodiment of the invention, ultrasound is transmitted in cycles of treating and monitoring. For instance, each cycle contains a first period, wherein ultrasound is applied with a first set of parameters, designed to stiffen the plaque, and then, for a second period with a second set of parameters, designed to monitor plaque stiffening. Optionally, there is some predetermined delay between the first and second periods. Optionally, during the delay, no ultrasound is applied to the abnormality. Treatment parameters and monitoring parameters are described below.

The ultrasound heating required for substantial crosslinking of collagen varies with US frequency and intensity. For instance, for continues (CW) sonication with frequency 20 MHz, and intensity of 2 W/cm$^2$, heating 2 minutes may be required.

Ultrasonic Treatment Parameters for Stabilization of Blood Vessel Wall Abnormality Following are definitions of treatment parameters that are used in the description below:

Frequency is the frequency of the vibrational (ultrasonic) energy.

Intensity is the vibrational energy applied power divided by the surface on which this power is measured/applied.

Duration of treatment is defined as the actual time during which vibrational energy is being applied to the arterial wall.

Elapsed treatment time is the time difference between the initiation and termination of treatment, elapsed treatment time is also referred herein as heating period, and includes the time it takes for the temperature to get to therapeutic values and the time it remains at such values;

Burst length, is the length of time for a single burst of vibrational energy; and Pulse repetition frequency (PRF) is the number of pulses applied per time unit, usually expressed in Hz.

Optionally, the vibrational energy is applied in a continuous (CW) mode for periods of 1-100 seconds, depending on the other parameters as described below.

Alternatively, the vibrational energy is applied in several bursts of energy, interspersed in relatively long periods of no energy output.

Broad, preferred, and exemplary values for each of these parameters is set forth in the following table:

| PREFERRED AND EXEMPLARY TREATMENT CONDITIONS | | | |
|---|---|---|---|
| | BROAD | PREFERRED | EXEMPLARY |
| Intensity (SPT, W/cm$^2$) | 1-10000 | 1-5000 | 1-1000 |
| Frequency (MHz) | 1-100 | 1-50 | 10-40 |
| Elapsed Time (sec.) | 0.1-1000 | 0.2-600 | 0.5-300 |
| Duty Cycle (%) | 0.01-100 | 0.1-100 | 0.1-100 |
| Pulse Repetition Frequency (PRF) (Hz) | 0.1-10000 | 0.1-1000 | 0.1-100 |

Ultrasonic Parameters for Monitoring Stiffening

| PREFERRED AND EXEMPLARY TREATMENT PROGRESSION MONITORING | | | |
|---|---|---|---|
| | BROAD | PREFERRED | EXEMPLARY |
| Intensity (SPT, W/cm$^2$) | 0.001-10 | 0.01-5 | 0.1-0.750 |
| Frequency (MHz) | 1-100 | 1-50 | 10-40 |
| Elapsed Time (sec.) | 0.00001-1 | 0.0001-0.01 | 0.0001-0.002 |
| Duty Cycle (%) | 0.01-100 | 0.01-80 | 00.1-50 |

Expected Effect of Treatment Parameters on Treatment Results:

(1) Frequency: Living tissue absorb ultrasound of higher frequency better than that of lower frequency, typically monotonic in all the mentioned ranges. Higher energy absorption is associated with more efficient heating, that is, more of the ultrasound energy is absorbed in the tissue and generates heating of the tissue. Additionally, higher energy absorption (and therefore also higher frequency of ultrasound) is associated with less penetration of the ultrasound energy to deep tissue layers, as much of the energy is absorbed in the outer layers. Accordingly, higher frequency is also associated with fast stiffening of outer tissue layers and more pronounced self-containment of the heating process.

(2) Intensity: Higher intensity causes deposition of more heat, which results in faster elevation of the temperature.

(3) Elapsed time: longer elapsed time, at equal burst length and pulse frequency, is associated with increased heating of the tissue.

Treatment Control

Figure 11:
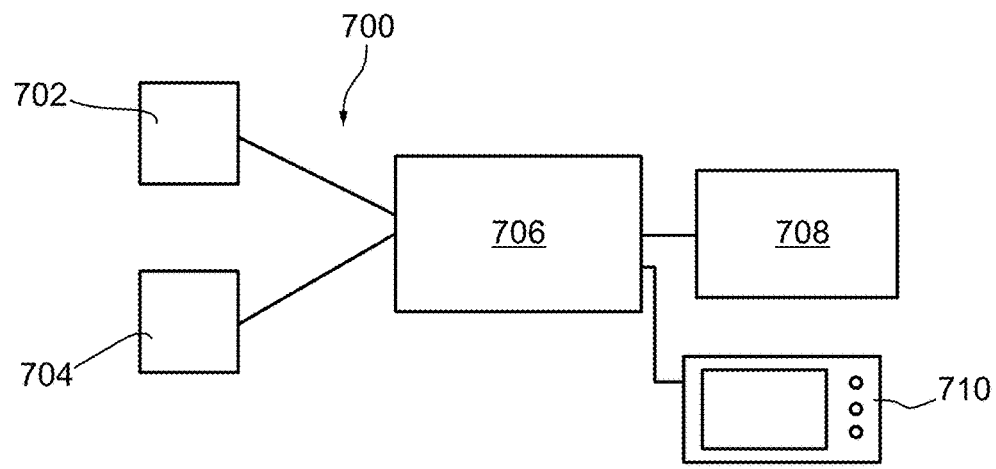
FIG. 11 is a block diagram of an apparatus for treating vulnerable plaque in accordance with an embodiment of the invention.

FIG. 11 is a schematic illustration of an apparatus 700 for treating vulnerable plaque or aneurysm. Apparatus 700 includes an ultrasound emitter 702; an ultrasound receiver 704; and a controller 706. Optionally, controller 706 is configured to stop ultrasound emission by emitter 702 upon receiving ultrasound signal with a predetermined parameter from ultrasound receiver 704.

In an embodiment of the invention, the predetermined parameter is a backscatter coefficient of the reflections from the tissue. This coefficient is measured during treatment, and maximal crosslinking is assumed when it stops increasing.

In an embodiment of the invention, the predetermined parameter is a ratio between intensity of ultrasound emission received by receiver 704 before treatment, and intensity of ultrasound emission received by the same receiver at the time of control. For instance, in an embodiment of the invention the controller is configured to stop the emission when the intensity of received ultrasound is at least 5 times larger than it was before treatment.

Optionally, there are many different ultrasound receivers and/or many ultrasound emitters in an apparatus 700. Optionally, the receivers are arranged in a cylindrical, outward facing array and are mounted on a catheter.

Figure 12A:
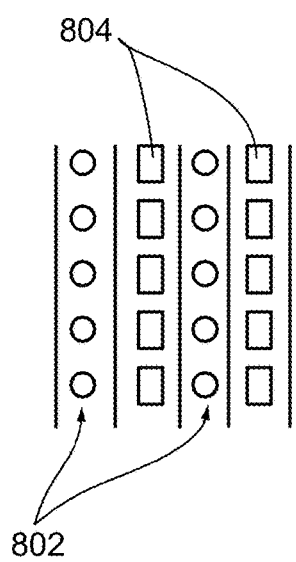
FIG. 12A and FIG. 12B are schematic illustrations of arrays of ultrasound emitters and receivers according to embodiments of the present invention.
Figure 12B:
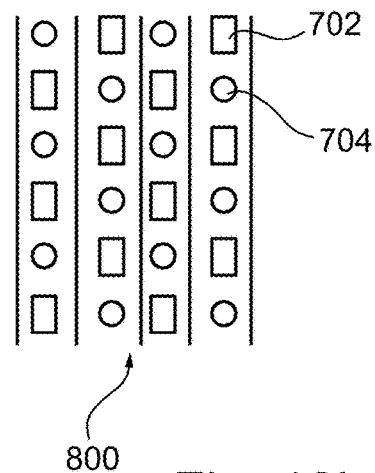

In an embodiment of the invention, illustrated in FIG. 12A, there are separate arrays of emitters (802) and separate arrays of receivers (804). In an embodiment of the invention, illustrated in FIG. 12B, an annular array 800 includes receivers (704) and emitters (702).

Preferably, a same ultrasound element functions as an emitter or as a receiver, depending on a command received from controller 706. Optionally, controller 706 may control all the elements to emit treating ultrasound for a certain period, and then one or more to emit monitoring ultrasound, and one or more to receive the monitoring ultrasound for a certain period. Preferably, in the monitoring stage, one device emits ultrasound and all the other ones receive reflections from the tissue. The monitoring period may be the same as or different from the treating period. A rest period may be present between treating period and monitoring period and/or between treatment period and monitoring period. Each period may be controlled to be of any desired length, for instance 10 ms, 50 ms, 500 ms. Optionally, length of emission period, receipt period, and delay period are controllable independently of each other.

Optionally, controller 706 assigns some of the ultrasound devices to function as emitters and some to function as receivers, and changes these assignments during treatment and detection.

Optionally, device 700 also includes a manual control 708. The manual control may be configured to allow a user, for instance, a physician operating the device, to control the device. Some examples of control possibilities that manual control may allow for are start treatment, stop treatment, set ultrasound detection parameters, set ultrasound treatment parameters, set ultrasound detection parameters, etc. In this context, treatment parameters are the characteristic of the treatment ultrasound, such as intensity, frequency, and pulse repetition, and ultrasound detection parameters may be similar characteristic of ultrasound used for monitoring the stiffness, as well as characteristics of the receivers, for instance: gain, frequency, etc.

Optionally, each of the emitters (702) or (802) elements may be applied with electric energy in different times, in such a fashion that the total energy output may be focused in the tissue to one or several focal points, as presented, for instance, in US '210. Optionally, device 700 is configured to provide treatment in predetermined power/time settings, sp as to be useful in stiffening vessel wall without damaging nearby tissue. Optionally, ultrasound absorption is evaluated in situ based on received backscatter, and the settings are normalized respective to the detected energy attenuation.

In operation, device 700 is mounted on a catheter configured for insertion into blood vessel. The catheter is advanced in the blood vessel when device 700 is in a detection mode, such that all the detectors are on. Optionally, the detected signals are analyzed to present to a display unit 710 echo images of the blood vessel. When blood vessel wall abnormality is identified (for instance, by an operator viewing images displayed on unit 710, by an automatic image analyzer (not shown) in communication with controller 706, etc) the catheter location is set mechanically, and turned into treatment mode.

In treatment mode, ultrasound emitters that face the identified plaque or aneurysm start operating to treat the abnormality by irradiating it with ultrasound having treatment parameters as discussed above. Ultrasound emitters facing other portions of the blood vessel may be shut off, or continue working in detection mode to allow immediate identification of any change in tissue structure that may be unintentionally caused by treatment of the nearby tissue.

After a period of applying treating ultrasound, the emitters are switch to emit ultrasound of monitoring parameters as discussed above, and receiving ultrasound signals received from the tissue. These may be ultrasound signals reflected or scattered from the tissue. The received signals are analyzed by a processor, which is optionally inside controller 706 or in communication therewith, and when the processor analyzes the received signals to indicated sufficient tissue stiffening, controller 706 control stoppage of the treatment.

Optionally, echo data of the treated area is then obtained and presented at display 710, to allow an operator to decide whether to continue treatment, optionally with other stopping parameters, to finish operation, to treat other portion of same plaque or aneurysm, or to continue searching for other abnormalities.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Furthermore, the terms "comprise," "include," "have" and their conjugates, shall mean, when used in the disclosure and/or claims, "including but not necessarily limited to."

It is noted that some of the above described embodiments may describe the best mode contemplated by the inventors and therefore may include structure, acts or details of structures and acts that may not be essential to the invention and which are described as examples. Structure and acts described herein are replaceable by equivalents, which perform the same function, even if the structure or acts are different, as known in the art. Therefore, the scope of the invention is limited only by the elements and limitations as used in the claims.

EXAMPLE

Ultrasonic Heating of Pig Aorta to Collagen Denaturation
General Experiment Description:
Pieces of pig aorta where heated by ultrasonic irradiation to a level that caused collagen denaturation in the irradiated region.
Tissue Samples Preprocessing:
Fresh aorta specimens from heart exit 25 mm long.
Male domestic pigs, 6 months old, 90 Kg. Lahav Research Institute (Lahav, Israel).
The harvested fresh aortas were kept in a sealed bag in freezing at (−20)C until the experiment (maximal 30 days).
About 6-8 hours prior to the experiment, the target aorta was defrosted in room temperature.

Each aorta was sliced along the lumen longitudinal axis and cut to pieces of 50×30 mm.

Experimental Setup:

The aorta tissue samples were positioned standing in a big bath (150×100×100) filled with PBS at room temperature.

Ultrasonic transducer used: 10 MHz, plate piezzo-element, 3 mm diameter, non-focused.

The ultrasonic transducer was positioned facing the center of the tissue sample towards the intima face, 10 mm from the tissue (to avoid heating effects from the heating of the transducer during work)

Experimental Protocol:

For each sample, the ultrasonic transducer was applied continues excitation for 5 minutes. After each sonication, the transducer was allowed to cool for about 10 minutes.

| | |
|---|---|
| Intensity (SPT, W/cm$^2$) | 1 |
| Frequency (MHz) | 10 |
| Elapsed Time (sec.) | 300 |
| Duty Cycle (%) | 100 (continuous) |
| Pulse Repetition Frequency (PRF) (Hz) | Not applicable |

Samples Processing:

Immediately after the sonication, each aorta segments was fixed for 24 hours in 5% formalin and embedded in paraffin.

Serial sections, each five 5 um thick, were cut from all segments and stained with Hematoxylin & Eosin.

Figure 13:
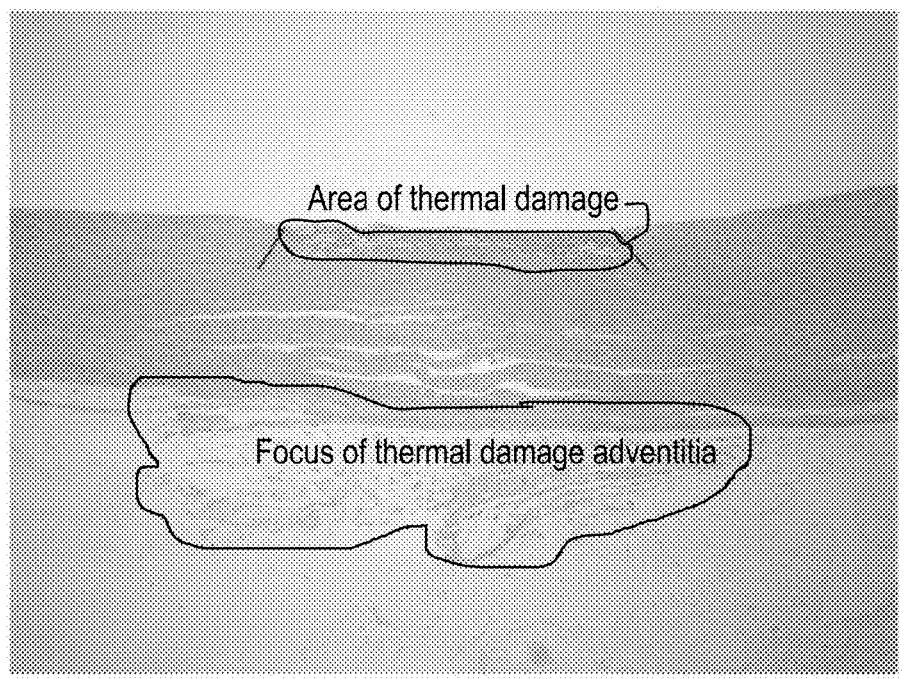
FIGS. 13 and 14 are photographs of artery portions treated in accordance with an embodiment of the invention.
Figure 14:
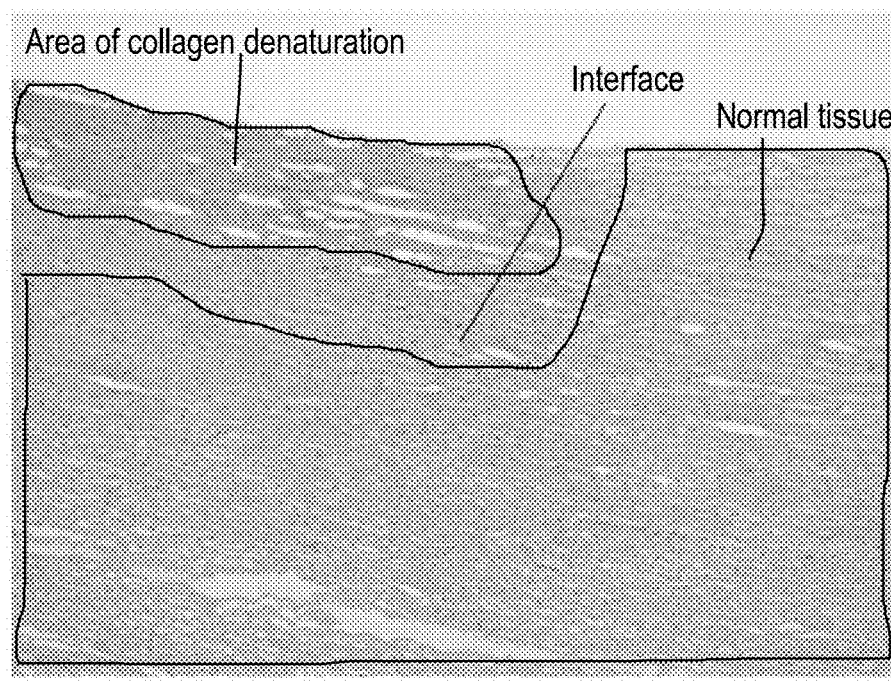

Results:

FIGS. 13 and 14 show exemplary 5 μm thick sections of an artery treated as described above.

The heating foci were observed on macro.

There is clumping of elastic fibers towards the inner third of the tunica media, near the intima.

The heating foci consist of a well demarcated area of necrosis (typical thermal damage with apparent protein clotting) in the adventitia.

Above this area (in the middle part of the media), there is a focal area of elastic fiber separation and fragmentation.

Dimensions of area of fiber clumping and vacuolation for exemplary samples:

In general, the foci of clumping and vacuolation, interpreted as thermal damage, were present in the inner third of the media, (e.g. from the intima into the media).

Approximate average dimensions of the fiber clumping area observed per section were length of 2.7±0.3 mm and depth from intima of 1.8±0.2 mm.

The samples do not exhibit any change in refringentcy or coloration of the elastic fibers throughout. This finding may be explained in that the elastic fibers are made of Elastin. Without being bound to theory, It is assumed that the clumping of the elastic fibers is caused by the cross-linking and shrinking of thin collagen fiber mesh that surrounds the thick Elastin fibers.

Apparent denaturation is clearly observed in the adventitia region.

What is claimed is:

1. A method of applying ultrasound energy to an inner surface of a blood vessel wall to treat a target tissue, the method comprising:
    providing an ultrasound emitter adapted to emit non-focused ultrasound energy, wherein said providing comprises selecting parameters of said energy to treat said target tissue when said emitter is positioned at a distance from an intima of said blood vessel;
    heating at least a portion of the target tissue located in an adventitia or further away from an intima of the blood vessel without causing thermal necrosis of said intima, using said non-focused ultrasound energy delivered intrabody, by positioning said ultrasound emitter at a distance from said intima selected for treating said target tissue using said energy, without said ultrasound emitter contacting said intima during said heating so as to allow blood flow between said emitter and said intima to cool non-targeted tissue.

2. A method according to claim 1, wherein said heating is configured to cause at least a portion of collagen in the heated blood vessel wall to become 100% cross-linked.

3. A method according to claim 1, wherein said heating is to a temperature of 60-80° C.

4. A method according to claim 1, wherein monitoring comprises elastography.

5. A method according to claim 4, wherein said elastography is ultrasound elastography.

6. A method according to claim 1, further comprising stopping said treatment when at least a portion of the blood vessel undergoes a desired mechanical modification.

7. A method according to claim 1, further comprising stopping said treatment when at least a portion of the blood vessel undergoes a desired biological modification.

8. A method according to claim 1, wherein said blood vessel is an artery.

9. A method according to claim 8, wherein said blood vessel wall target tissue is vulnerable plaque.

10. A method according to claim 8, wherein said blood vessel wall target tissue is aneurysm.

11. A method according to claim 1, wherein said heating causes full cross-linking of collagen in at least a portion of the heated blood vessel wall.

12. A method according to claim 1, wherein said heating causes at least 50% of the collagen of the target tissue to shrink in at least 50% of its length before heating.

13. A method according to claim 1, wherein said heating causes at least 50% of the collagen of the target tissue to maximally shrink.

14. A method according to claim 9, wherein said ultrasonically heating comprises stiffening of a vulnerable plaque tissue as to decrease the plaque's vulnerability to rupture.

15. A method according to claim 10, wherein said ultrasonically heating comprises stiffening of aneurysm tissue so as to decrease the tendency of the aneurysm to rupture.

16. A method according to claim 10, wherein ultrasonically heating comprises heating collagen sufficiently to shrink said collagen and reduce a diameter of the aneurysm.

17. A method according to claim 1, wherein ultrasonically heating comprises invasively applying ultrasound radiation to a portion of said blood vessel.

18. A method according to claim 17, wherein said ultrasound is applied from within the blood vessel having the target tissue.

19. A method according to claim 1, comprising deploying a stent in the blood vessel before said heating.

20. A method according to claim 1, wherein heating is for a period of between 0.1 and 1000 seconds.

21. A method according to claim 20, wherein heating is for a period of between 0.5 and 300 seconds.

22. An apparatus for applying ultrasound energy to an inner surface of a blood vessel to treat tissue comprising:
    a catheter;
    at least one ultrasound emitter mounted on the catheter and adapted for emitting non-focused ultrasound energy at a target tissue located in an adventitia or further away from an intima of the blood vessel, wherein parameters of said energy are selected to heat said target tissue when said emitter is positioned at a distance from said intima, said emitters arranged to face said intima and be positioned a distance away from said intima during emitting so as to allow blood flow between said emitter and said intima to cool non-targeted tissue; and a controller, wherein the controller is configured to control said ultrasound emission to heat said target tissue without causing thermal necrosis of said intima.

23. An apparatus according to claim 22, wherein a single ultrasound transducer is configured to cyclically receive and emit ultrasound.

24. An apparatus according to claim 22, comprising a manual control, configured to allow a user to control ultrasound emission parameters and/or ultrasound detection parameters.

25. An apparatus according to claim 22, configured to provide treatment using predetermined power/time settings, so as to stiffen said target tissue of the blood vessel.

26. An apparatus according to claim 22, configured to provide treatment using predetermined power/time settings, so as to block vasa vasorum.

27. A method according to claim 1, further comprising:
identifying vulnerable plaque in a blood vessel of the subject, the vulnerable plaque comprising a lipid pool and a cap, and wherein ultrasonically heating comprises heating said vulnerable plaque without congealing the lipid pool.

28. A method according to claim 27, wherein the vulnerable plaque comprises collagen, and said heating fully cross-links at least a portion of said collagen.

29. A method according to claim 1, further comprising:
(a) identifying said target tissue in said blood vessel of a subject; and
(b) stabilizing said target tissue by said heating.

30. A method according to claim 29, wherein said target tissue comprises vulnerable plaque.

31. A method according to claim 29, wherein said target tissue comprises aneurysm.

32. An apparatus according to claim 22, comprising a receiving circuit including at least one ultrasound receiving element, and wherein the controller is configured to stop ultrasound emission by the emitter upon receiving an ultrasound signal with a predetermined parameter value by the ultrasound receiving element.

33. An apparatus according to claim 32 wherein said parameter is ultrasound reflection.

34. An apparatus according to claim 33, wherein said ultrasound reflection comprises ultrasound reflection from said target tissue.

35. An apparatus according to claim 32, wherein the predetermined parameter is a ratio between intensity of a signal that is currently received and intensity of ultrasound that was received before treatment.

36. An apparatus according to claim 32, wherein the predetermined parameter value is a ratio between a rate at which a received signal is changing during the last time the signal was received and a rate at which a received signal was changing earlier in treatment.

37. An apparatus according to claim 32, wherein the predetermined parameter is related to changes that take place in said adventitia.

38. An apparatus according to claim 22, wherein said at least one ultrasound emitter is arranged to face outwardly towards the vessel wall.

39. An apparatus according to claim 22, wherein said catheter is configured to allow blood flow to cool non-targeted areas.

40. A method according to claim 1, further comprising monitoring a parameter related to a property of at least a portion of the heated portion of the blood vessel wall.

41. A method according to claim 40, further comprising stopping the heating when said parameter changes by a predetermined factor or after said parameter changes in a rate that is a predetermined fraction of a maximal rate change observed during heating.

42. A method according to claim 9, wherein heating comprises heating said vulnerable plaque without congealing a lipid pool in said vulnerable plaque.

43. A method according to claim 1, wherein said heating is configured to cause denaturation.

44. A method according to claim 1, wherein heating comprises treating an area or a volume of tissue located at least 2.0 mm from said intima.

45. A method according to claim 1, wherein said heating comprises heating sufficiently to cause thermal damage.

46. A method according to claim 1, wherein said heating comprises treating said target tissue without damaging nearby tissue.

47. A method according to claim 1, further comprising selecting a type of said target tissue to heat.

48. A method according to claim 40, wherein said parameter is related to a stiffness of a portion of the blood vessel.

49. A method according to claim 40, wherein said parameter is ultrasound reflection.

50. A method according to claim 40, wherein said parameter is ultrasound backscatter.

51. A method according to claim 40, wherein said parameter is related to a degree of cross-linking of collagen in at least a portion of the heated target tissue.

52. A method according to claim 1, wherein said blood vessel comprises a blood vessel wall.

53. An apparatus according to claim 32, wherein the ultrasound emitter and the ultrasound receiver are the same.

54. A method according to claim 1, wherein said non-focused ultrasound is delivered to said target tissue located along a portion of the circumference of the blood vessel.

55. A method according to claim 1, wherein said non-focused ultrasound is emitted at a frequency of 10-40 Mhz.

56. A method according to claim 1, wherein said target tissue is located a distance away from said intima of 1.6 mm to 2.0 mm.

57. A method according to claim 1, wherein said heating comprises heating such that blood flow along said vessel cools said intima.

58. An apparatus according to claim 22, wherein said emitter is rectangular and comprises a flat emitting surface.

* * * * *